United States Patent [19]
Cerelli et al.

[11] Patent Number: 5,620,861
[45] Date of Patent: Apr. 15, 1997

[54] METHOD AND KIT FOR PYRIDINIUM CROSSLINK ASSAY

[75] Inventors: Mary J. Cerelli, Burlingame; Hsin-Shan J. Ju, Cupertino; Robert F. Zuk, Burlingame, all of Calif.

[73] Assignee: Metra Biosystems, Inc., Mountain View, Calif.

[21] Appl. No.: 484,212

[22] Filed: Jun. 7, 1995

Related U.S. Application Data

[63] Continuation-in-part of Ser. No. 37,602, Mar. 26, 1993, abandoned, Ser. No. 209,924, Mar. 11, 1994, abandoned, PCT/US93/12321, Dec. 17, 1993, abandoned, Ser. No. 140,284, Oct. 20, 1993, abandoned, Ser. No. 992,936, Dec. 17, 1992, abandoned, and Ser. No. 992,888, Dec. 17, 1992, abandoned, said Ser. No. 37,602, is a continuation-in-part of Ser. No. 992,888, and Ser. No. 922,906, Jul. 31, 1992, abandoned.

[51] Int. Cl.$^6$ .......................... G01N 33/53; G01N 33/543
[52] U.S. Cl. .......................... 435/7.9; 435/7.92; 435/7.93; 435/7.94; 435/70.21; 435/810; 435/975; 436/512; 436/518; 436/530; 436/531; 436/86; 530/387.1; 530/387.9; 530/389.1; 530/391.1; 530/391.3
[58] Field of Search .......................... 435/7.1, 7.9, 7.92, 435/7.94, 70.21, 240.26, 240.27, 810, 975, 7.13; 436/512, 518, 530, 531, 86, 87, 161, 528; 530/387.1, 387.9, 389.1, 391.1, 391.3, 391.5, 391.7

[56] References Cited

U.S. PATENT DOCUMENTS

| | | | |
|---|---|---|---|
| 4,973,666 | 11/1990 | Eyre | 530/323 |
| 5,004,806 | 4/1991 | Kung | 530/415 |
| 5,140,103 | 8/1992 | Eyre | 530/327 |
| 5,527,715 | 6/1996 | Kung et al. | 436/547 |

FOREIGN PATENT DOCUMENTS

| | | |
|---|---|---|
| 0556152A1 | 1/1993 | European Pat. Off. . |
| WO89/04491 | 5/1989 | WIPO . |
| WO89/12824 | 12/1989 | WIPO . |
| WO91/10141 | 7/1991 | WIPO . |

OTHER PUBLICATIONS

Beardsworth, L.J., et al., "Changes with Age in the Urinary Excretion of Lysyl—and Hydroxylsylpyridinolie, Two New Markers of Bone Collagen Turnover," *J. Bone and Mineral Res.* 5(7): 671–676 (1990).

Black, D., et al., "Quantitative Analysis of the Pyridinium Crosslinks of Collagen in Urine Using Ion–Paired Reversed–Phase High–Performance Liquid Chromatography," *Anal. Biochem.* 169:197–203 (1988).

Black, D., et al., "Urinary Excretion of the Hydroxypyridinium Crosslinks of Collagen in Patients with Rheumatoid Arthritis," *Ann. Rheumat. Dis.* 48:641–644 (1989a).

Black, D., et al., "Excretion of Pyridinium Cross–Links in Ovariectomized Rats as Urinary Markers for Increased Bone Resorption," *Calcif. Tissue Int.* 44: 343–347 (1989b).

Body, J.J., and Delmas, P.D., "Urinary Pyridinium Cross–Links as Markers of Bone Resorption in Tumor–Associated Hypercalcemia," *J. Clinical Endocrin. and Metab.* 74(3):471–475 (1992).

(List continued on next page.)

*Primary Examiner*—Lora M. Green
*Assistant Examiner*—Susan C. Wolski
*Attorney, Agent, or Firm*—Vincent M. Powers; Peter J. Dehlinger

[57] ABSTRACT

A method of assaying bone collagen degradation activity in a human subject. In the method, a human urine sample is reacted with an antibody which (i) is capable of reacting immunospecifically with pyridinium crosslinks selected from the group consisting of native free pyridinoline and native free deoxypyridinoline, and (ii) has a ratio of reactivity toward the selected pyridinium crosslinks and urinary pyridinium peptides larger than 1,000 daltons in molecular weight, of greater than about 5:1. An immunocomplex forms between the antibody reagent and the selected pyridinium crosslinks which are present in the sample, and the amount of immunocomplex is measured. Also disclosed are antibody reagents and kits which can be used in the method.

7 Claims, 4 Drawing Sheets

OTHER PUBLICATIONS

Coleman, R.E., et al., "Preliminary Results of the Use of Urinary Excretion of Pyridinium Crosslinks for monitoring Metastatic Bone Disease," *Br. J. Cancer* 65:766–768 (1992).

Demers, L.M., "New Biochemical Marker for Bone Disease: Is it a Breakthrough?" *Clin. Chem.* 38(11):2169–2170 (1992).

Eyre, D., et al., "Editorial: New Biomarkers of Bone Resorption," *J. Clin. Endocrin. and Metab.* 74(3):470A–470C (1992).

Eyre, D., et al., "Identification of Urinary Peptides Derived from Crosslinking Sites in Bone Collagen in Paget's Disease," *J. Bone & Min. Res.* 3(1):S210, Abstract No. 565 (1988).

Eyre, D.R., et al., "Quantitation of Hydroxypyridinium Crosslinks in Collagen by High–Performance Liquid Chromatography," *Anal. Biochem.* 137:380–388 (1984).

Fujimoto, D., et al., "Isolation and Characterization of a Fluorescent Material in Bovine Achilles Tendon Collagen," *Biochem. & Biophys. Res. Commun.* 76(4):1124–1129 (1977).

Fujimoto, D., et al., "The Structure of Pyridinoline, a Collagen Crosslink," *Biochem. & Biophys. Res. Commun.* 84(1):52–57 (1978).

Fujimoto, D., and Moriguchi, T., "Pyridinoline, a Non–Reducible Crosslink of Collagen," *J. Biochem.* 83:863–867 (1978).

Fujimoto, D., et al., "Analysis of Pyridinoline, a Cross–Linking Compound of Collagen Fibers, in Human Urine," *J. Biochem.* 94:1133–1136 (1983).

Gunja–Smith, Z., and Boucek, R.J., "Collagen Cross–Linking Compounds in Human Urine," *Biochem. J.* 197:759–762 (1981).

Hanson, D.A., et al., "A Specific Immunoassay for Monitoring Human Bone Resorption: Quantitation of Type I Collagen Cross–Linked N–Telopeptides in Urine," *J. Bone and Mineral Res.* 7(11):1251 (1992).

Kollerup, G., et al., "Quantitation of Urinary Hydroxypyridinium Cross–Links from Collagen by High–Performance Liquid Chromatography," *Scand. J. Clin. Lab. Invest.* 52:657–662 (1992).

Macek, J., and Adam, M., "Determination of Collagen Degradation Products in Human Urine in Osteoarthrosis," *Z. Rheumatol.* 46:237–240 (1987).

Ogawa, T., et al., "A Novel Fluor in Insoluble Collagen: A Crosslinking Moiety in Collagen Molecule," *Biochem. & Biophys. Res. Commun.* 107(4):1252–1257 (1982).

Ohishi, T., et al., "Quantitative Analyses of Urinary Pyridinoline and Deoxypyridinoline Excretion in Patients with Hyperthyroidism," *Endocrin. Res.* 18(4):281–290 (1992).

Paterson, C.R., et al., "Pyridinium Crosslinks as Markers of Bone Resorption in Patients with Breast Cancer," *Br. J. Cancer* 64:884–886 (1991).

Robins, S.P., "An Enzyme–Linked Immunoassay for the Collagen Cross–Link Pyridinoline," *Biochem. J.* 207:617–620 (1982).

Robins, S.P., "Turnover and Crosslinking of Collagen," in *Collagen in Health and Disease* (Weiss, J.B., et al., Eds.) Churchill Livingston, Edinburgh, Scotland, pp. 160–178 (1982).

Robins, S.P., "Cross–Linking of Collagen," *Biochem. J.* 215:167–173 (1983).

Robins, S.P., and Duncan, A., "Cross–Linking of Collagen," *Biochem. J.* 215:175–182 (1983).

Robins, S.P., et al., "Measurement of the Cross Linking Compound, Pyridinoline, in Urine as an Index of Collagen Degradation in Joint Disease," *Ann. Rheumat. Dis.* 45:969–973 (1986).

Robins, S.P., and Duncan, A., "Pyridinium Crosslinking of Bone Collagen and Their Location in Peptides Isolated from Rat Femur," *Biochim. et Physiophys. Acta* 914:233–239 (1987).

Seibel, M.J., et al., "Urinary Hydroxy–Pyridinium Crosslinks Provide Indices of Cartilage and Bone Involvement in Arthritic Diseases," *J. Rheumatol.* 16(7):964–970 (1989).

Seibel, M.J., et al., "Urinary Pyridinium Crosslinks of Collagen: Specific Markers of Bone Resorption in Metabolic Bone Disease," *TEM* 3(7):263 (1992).

Wu, J.–J., and Eyre, D.R., "Identification of Hydroxypyridinium Cross–Linking Sites in Type II Collagen of Bovine Articular Cartilage," *Biochemistry* 23:1850–1857 (1984).

METHOD AND KIT FOR PYRIDINIUM CROSSLINK ASSAY

This application is a continuation-in-part of Ser. No. 08/037,602 filed Mar. 26, 1993, abandoned, which is a continuation-in-part of Ser. Nos. 07/992,888 filed Dec. 17, 1992 and 07/922,906 filed Jul. 31, 1992, both abandoned; a continuation-in-part of Ser. No. 08/209,924 filed Mar. 11, 1994, abandoned; and a continuation-in-part of International Application No. PCT/US93/12321 filed Dec. 17, 1993, abandoned, which is a continuation-in-part of Ser. Nos. 08/140,284 filed Oct. 20, 1993, 07/992,936 filed Dec. 17, 1992, 08/037,602 filed Mar. 26, 1993, and 07/992,888 filed Dec. 17, 1992, all abandoned.

1. FIELD OF THE INVENTION

The present invention relates to a method for determining native free pyridinium crosslink levels in human urine samples, and to an antibody reagent and kit for use in the method.

2. REFERENCES

Black, D., et al., *Anal. Biochem.* 169: 197–203 (1988).

Black, D., et al., *Annals of Rheumatic Diseases* 48: 641–644 (1989).

Brown, J. P., et al., *Lancet* 1091–1093 (1984).

Cook, J., et al., *Ann. Clin. Biochem.* 12: 219 (1975).

Daniloff, Y., et al., *Connect. Tissue. Res.* 27: 187 (1992).

Eyre, D. R., et al., *Anal. Biochem.* 137: 380–388 (1984).

Eyre, D. R., et al., *FEBS* 2: 337–341 (1987).

Fujimoto, D., et al., *J. Biochem.* 83: 863–867 (1978).

Fujimoto, D., et al., *J. Biochem.* 94: 167–173 (1983).

Gosling, J., *Clin. Chem.* 36 (8): 1408 (1990).

Gunja-Smith, Z., et al., *Biochem. J.* 197: 759–762 (1981).

Harlow, E., et al., Antibodies: A Laboratory Manual, Cold Spring Harbor Lab (1988).

Henkel, W., et al., *Eur. J. Biochem.* 165: 427–436 (1987).

Macek, J., et al., *Z. Rheumatol.* 46: 237–240 (1987).

Ogawa, T., et al., *Biochem. Biophys. Res. Commune.* 107: 1251–1257 (1982).

Robins, S. P., *Biochem J.* 207: 617–620 (1982a).

Robins, S. P., in "Collagen in Health and Disease" (Weiss, J. B., et al., eds.) pp. 160–178, Churchill Livingstone, Edinburgh (1982b).

Robins, S. P., *Biochem. J.* 215: 167–173 (1983).

Robins, S. P., et al., *Ann. Rheumatic Dis.* 45: 969–973 (1986).

Robins, S. P., et al., *Biochim. Biophys. Acta.* 914: 233–239 (1987).

Seibel, et al., *J. Rheumatol* 16: 964–970 (1989).

Wong, S. S., *Chemistry of Protein Conjugation and Cross-Linking*, CRC Press, Boca Raton, Fla. (1991).

3. BACKGROUND OF THE INVENTION

There are a variety of conditions in humans which are characterized by a high level of bone resorption and by an abnormal balance between bone formation and bone resorption. Among the more common of these are osteoporosis, Paget's disease, and conditions related to the progress of benign and malignant tumors of the bone and metastatic cancers which have been transferred to bone cells from, for example, prostate or breast initial tumors. Other conditions which are associated with changes in collagen metabolism include osteomalacial diseases, rickets, abnormal growth in children, renal osteodystrophy, and a drug-induced osteopenia. Irregularities in bone metabolism are often side effects of thyroid treatments and thyroid conditions per se, such as primary hypothyroidism and thyrotoxicosis as well as Cushing's disease.

It has been recognized that disorders of bone resorption or other conditions characterized by an abnormal balance between bone formation and bone resorption can be detected by altered levels of pyridinium crosslinks in urine (Robins, 1982b; Macek; Black). The crosslinks, which originate from a number of collagen-containing tissues, take the form of compounds containing a central 3-hydroxy pyridinium ring in which the ring nitrogen is derived from the epsilon amino group of either lysine or hydroxylysine (Fujimoto, 1978; Robins, 1982a; Gunja-Smith; Ogawa; Eyre).

The pyridinium crosslink compounds found in urine can be grouped into four general classes: (1) free, native crosslinks having a molecular weight of about 400 daltons (Fujimoto), (2) glycosylated crosslinks and crosslink peptide forms having a molecular weight of between about 550 and 1,000 daltons (Robins, 1983), (3) crosslink peptide forms having a molecular weight between 1,000 and 3,500 daltons (Robins, 1983, 1984, 1987; Henkel; Eyre), and (4) crosslink peptide forms having a molecular weight greater than 3,500 daltons. In normal adult, these forms account for about 38% (1), 40% (2), 15% (3), and 7% (4) of total urinary crosslinks (Daniloff). About 80% of the free crosslinks (group 1 above) in normal adult urine is pyridinoline (Pyd), the ring nitrogen of which derives from hydroxylysine, and about 20% is deoxypyridinoline (Dpd), the ring nitrogen of which derives from lysine. This Pyd/Dpd ratio applies roughly to the other three classes of crosslinks in urine. The higher molecular weight crosslinks can be converted to free crosslinks by acid hydrolysis (Fujimoto, 1978).

Methods for measuring pyridinium crosslinks in urine have been proposed. One of these methods involves the measurement of total hydrolysed Pyd, i.e., Pyd produced by extensive hydrolysis of urinary crosslinks, by quantitating the hydrolysed Pyd peak separated by HPLC (Fujimoto, 1983). The relationship between total hydrolysed Pyd to age was determined by these workers as a ratio to total hydrolysed Pyd/creatinine, where creatinine level is used to normalize crosslink levels to urine concentration and skeletal mass. It was found that this ratio is high in the urine of children, and relatively constant throughout adulthood, increasing slightly in old age. The authors speculate that this may correspond to the loss of bone mass observed in old age.

Studies on the elevated levels of total crosslinks in hydrolyzed urine of patients with rheumatoid arthritis has been suggested as a method to diagnose this disease (Black, 1989). The levels of total hydrolyzed crosslinks for patients with rheumatoid arthritis (expressed as a ratio of total crosslinks measured by HPLC to creatinine) were elevated by a factor of 5 as compared to controls. However, only total hydrolysed Pyd, but not total hydrolysed Dpd, showed a measurable increase.

In a more extensive study using hydrolyzed urines, Seibel et al. showed significant increases in the excretion of Pyd and Dpd crosslinks relative to controls in both rheumatoid and osteoarthritis. The most marked increases for Pyd crosslinks were in patients with rheumatoid arthritis (Seibel).

Assay methods, such as those just noted, which involve HPLC quantitation of crosslinks from hydrolysed samples, or crosslink subfractions from non-hydrolysed samples, are relatively time-consuming and expensive to carry out, and may not be practical for widespread screening or monitoring therapy in bone-metabolism disorders.

Immunoassays have also been proposed for measuring urinary crosslinks. U.S. Pat. No. 4,973,666 discloses an assay for measuring bone resorption by detection in urine of specific pyridinium crosslinks, characterized by specific peptide extensions, associated with bone collagen. Two specific entities having peptide extensions presumed to be associated with bone collagen are described. These are obtained from the urine of patients suffering from Paget's disease, a disease known to involve high rates of bone formation and destruction. The assay relies on immunospecific binding of crosslink compounds containing the specific peptide fragment or extension with an antibody prepared against the crosslink peptide. It is not clear whether and how the concentration of crosslink peptide being assayed relates to total urinary crosslinks.

Robins has described a technique for measuring pyridinoline in urine by use of an antibody specific to hydrolysed Pyd (Robins, 1986). The method has the limitation that the antibody was found to be specific for the hydrolyzed form of Pyd, requiring that the urine sample being tested first be treated under hydrolytic conditions. The hydrolytic treatment increases the time and expense of the assay, and precludes measurements of other native pyridinium crosslinks.

The pyridinium crosslink content of collagen-containing tissues is known to vary in amount and composition according to tissue type. Pyd crosslinks are found in cartilage, bone, intervertebral discs, ligaments, and the aorta. Dpd crosslinks, which are generally less prevalent than Pyd crosslinks, are found in bone, dentine, ligaments, and the aorta. The proportion of Dpd in tissue pyridinium crosslinks appears to be highest in bone, which has a Pyd:Dpd ratio of between about 3:1 and 4:1. Pyridinium crosslinks in cartilage, on the other hand, contain predominantly Pyd.

Ideally, an assay method for assessing bone metabolism, based on pyridinium crosslink levels in urine, should (a) employ a non-hydrolysed urine sample, to avoid the need for acid hydrolysis of the sample, and (b) utilize an antibody reagent to detect native free pyridinium species, for reducing the time and expense of analysis over conventional HPLC-based tests.

4. SUMMARY OF THE INVENTION

The present invention provides an antibody reagent which is specific for native free pyridinoline, native free deoxypyridinoline, or both. The antibody may be polyclonal or monoclonal.

In one aspect, the invention includes a method of assaying bone collagen degradation activity in a human subject. In the method, a urine sample from the subject is reacted with a antibody which is capable of reacting immunospecifically with pyridinium crosslinks selected from the group consisting of native free pyridinoline and native free deoxypyridinoline. The antibody has a ratio of reactivity toward the selected pyridinium crosslinks and urinary pyridinium peptides larger than 1,000 daltons in molecular weight, of greater than about 5:1.

In one embodiment, the antibody is specific for native free pyridinoline, and has a ratio of reactivity toward native free pyridinoline and native free deoxypyridinoline of greater than about 5:1. In a second embodiment, the antibody is specific for native free deoxypyridinoline, and has a ratio of reactivity toward native free deoxypyridinoline and native free pyridinoline of greater than about 25:1. In another embodiment, the antibody is specific for both native free pyridinoline and native free deoxypyridinoline and has a ratio of reactivity toward native free pyridinoline and native free deoxypyridinoline of between about 2:1 and 1:2.

More generally, the ratio of reactivity toward native free pyridinoline and native free deoxypyridinoline can be from greater than 5:1 to less than 1:25, including all ratios in between.

The urine sample may be passed through a nitrocellulose filter or other suitable separation medium to remove sample components (e.g., proteins) which may interfere with the assay.

In another aspect, the invention includes an antibody reagent for use in the method. The antibody reagent is characterized by immunospecific binding to free pyridinium crosslinks selected from the group consisting of native free pyridinoline, native free deoxypyridinoline, or both, and a ratio of reactivity toward the selected pyridinium crosslinks and urinary pyridinium peptides larger than 1,000 daltons in molecular weight of greater than about 5:1.

The invention also includes an immunogen for use in preparing an antibody reagent such as described above. The immunogen consists of free Pyd or free Dpd, in either native or hydrolyzed form, coupled to a protein carrier, preferably by a water-soluble carbodiimide. One preferred protein carrier is keyhole limpet hemocyanin.

Also forming part of the invention is a method for producing monoclonal antibodies for use in the antibody reagent described above. The method includes forming a hybridoma composed of the fusion product of (a) spleen cells from an animal immunized with free pyridinoline or free deoxypyridinoline attached to a carrier protein, and (b) an immortalizing fusion partner, and selecting hybridomas which are immunoreactive with the selected native free pyridinium crosslinks. The free pyridinium crosslinks attached to the carrier protein can be native or hydrolysed in form.

In another aspect, the invention includes a kit for use in assaying bone collagen degradation levels in a human subject. The kit includes an antibody reagent which is capable of reacting immunospecifically with pyridinium crosslinks selected from the group consisting of native free pyridinoline, native free deoxypyridinoline, or both, and has a ratio of reactivity toward the selected pyridinium crosslinks and urinary pyridinium peptides larger than 1,000 daltons in molecular weight, of greater than about 5:1. The kit also includes detection means for detecting the amount of immunocomplex formed by reaction of the antibody reagent with free pyridinium crosslinks in the sample.

Preferably, the detection means includes a reporter enzyme which is effective to produce a colorimetric signal, although other formats can be used.

In one general embodiment, the kit includes a solid-phase support having a surface-attached binding agent which may an antibody reagent such as described above, or native free pyridinium crosslinks.

In another aspect, the invention includes an assay for quantitating a urinary analyte. In the assay, a urine sample is filtered through a membrane which is effective to remove substance(s) that bind non-specifically to antibodies while allowing the analyte to pass through. The filtered urine sample is reacted with a binding reagent effective to form an antigen-antibody complex with the analyte, under conditions effective to bind the antibody to the solid support in proportion to the amount of analyte in the sample. Preferred filter membrane include nitrocellulose, Immobilon-CD, and Immobilon-SPQ.

These and other objects and features of the invention will become more fully apparent when the following detailed description of the invention is read in conjunction with the accompanying drawings.

DETAILED DESCRIPTION OF THE INVENTION

I. Definitions

Figure 1A:
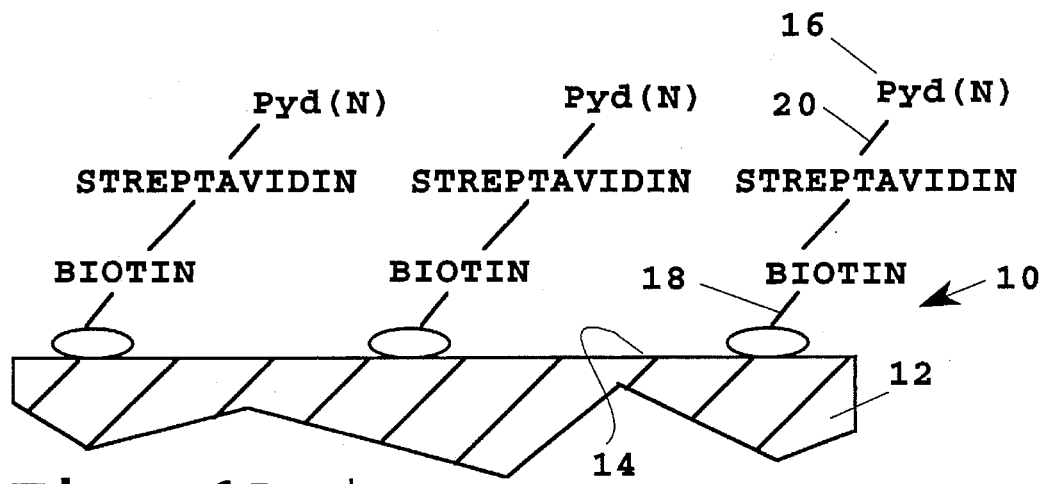
FIGS. 1A–1C illustrate steps in practicing an embodiment of an assay in accordance with the invention.

As used herein, the terms below have the following definitions:

"Pyd" or "pyridinoline" or "free pyridinoline" refers to the crosslink compound shown at I below, where the ring nitrogen is derived from the ε amino group of a hydroxylysyl residue, and "Dpd" or "deoxypyridinoline" or "free deoxypyridinoline" refers to the crosslink compound shown at II below, where the ring nitrogen is derived from the ε amino group of a lysyl residue.

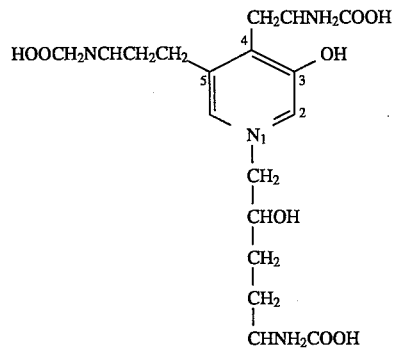

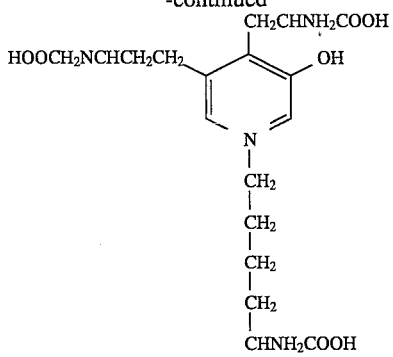

"Free crosslinks" refers to either compounds I or II or a mixture of the two.

"Glycosylated pyridinoline" or "glyco-Pyd" refers to glycosylated forms of compound I, wherein glycosyl groups are covalently bound to the aliphatic hydroxyl group of Pyd. Two glyco-Pyd crosslinks which have been identified are Gal-Pyd and Glc-Gal-Pyd, which contain the acetals shown at III and IV below, respectively.

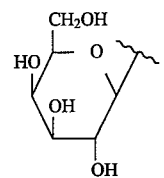

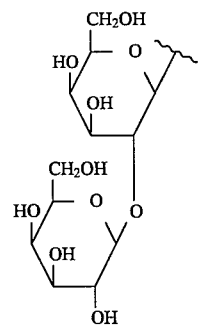

"Pyd-peptides" or "pyridinoline-peptides" refers to peptide-derivatized forms of compound I, in which one or more of the three amino acid residues in the compound is linked via a peptide linkage to additional amino acid residues. Similarly, "Dpd-peptides" or "deoxypyridinoline-peptides" refers to peptide-derivatized forms of compound II, in which one or more of the three amino acid residues in the compound is linked via a peptide linkage to additional amino acid residues.

"Pyridinium-peptides" refers to a mixture of Pyd-peptides and Dpd-peptides.

"Pyd-peptides having a molecular weight greater than 1000 daltons" or "Pyd-peptides (MW>1000)" refers to Pyd-peptides retained by a dialysis membrane having a 1,000 molecular weight cutoff.

"Dpd-peptides having a molecular weight greater than 1000 daltons" or "Dpd-peptides (MW>1000)" refers to Dpd-peptides retained by a dialysis membrane having a 1,000 molecular weight cutoff.

"Pyd crosslinks" refers to the pyridinium crosslinks in urine which contain compound I either in free or derivatized form. Pyd crosslinks include Pyd, glyco-Pyd and Pyd-peptides. Similarly, "Dpd crosslinks" refers to the pyridinium crosslinks in urine which contain compound II either in free or derivatized form. "Dpd crosslinks" include Dpd and Dpd-peptides.

"Pyridinium crosslinks" refers to pyridinium crosslinks which contain compounds I and/or II in free and/or derivatized form.

"Total H-Pyd" refers to total hydrolysed Pyd produced by hydrolyzing Pyd crosslinks to Pyd. Similarly, "total H-Dpd" refers to total hydrolysed Dpd produced by hydrolyzing Dpd crosslinks to Dpd.

"Hydrolysed-Pyd" or "H-Pyd" refers to Pyd produced by hydrolysing Pyd crosslinks in 6N HCl at 110° C. for 16 hours. Similarly, "Hydrolysed-Dpd" or "H-Dpd" refers to Dpd produced by hydrolysing Dpd crosslinks in 6N HCl at 110° C. for 16 hours.

"Native Pyd" or "N-Pyd" refers to Pyd obtained from urine which has not been subjected to hydrolytic conditions. Similarly, "native Dpd" or "N-Dpd" refers to free Dpd obtained from urine which has not been subjected to hydrolytic conditions.

An antibody (or antibody reagent) which is "capable of reacting immunospecifically with pyridinium crosslinks selected from the group consisting of native free pyridinoline and native free deoxypyridinoline" refers to a monoclonal antibody which is immunospecific for native free pyridinoline, native free deoxypyridinoline, or both, relative to other antigenic materials which may be present in urine samples. The ratio of reactivity (affinity) of the monoclonal antibody toward native free pyridinoline and native free deoxypyridinoline can range from about 5:1 or greater, to about 1:25 or less, including all ratios in between.

The meaning of "ratio of reactivity toward the selected pyridinium crosslinks and urinary pyridinium peptides larger than 1,000 daltons in molecular weight, of greater than about 5:1" depends on the relative specificities of the antibody for native free pyridinoline versus native free deoxypyridinoline. Where the antibody has a ratio of reactivity toward native free pyridinoline and native free deoxypyridinoline which is greater than 2:1, the quoted phrase refers to the ratio of reactivity toward N-Pyd and Pyd-peptides (MW>1000). Where the antibody has a ratio of reactivity toward native free pyridinoline and native free deoxypyridinoline which is less than 1:2, the quoted phrase refers to the ratio of reactivity toward N-Dpd and Dpd-peptides (MW>1000). For an antibody having a ratio of reactivity toward native free pyridinoline and native free deoxypyridinoline which is between or equal to 2:1 and 1:2, the quoted phrase means that the ratio of reactivity toward N-Pyd and Pyd-peptides (MW>1000) and also the ratio of reactivity toward N-Dpd and Dpd-peptides (MW>1000) are both greater than about 5:1.

II. Preparation of Antibody Reagent

This section describes the production of antibodies ("antibody reagent") which are specific for native free pyridinium crosslinks (either N-Pyd, N-Dpd, or both), as evidenced by a ratio of reactivity toward the native free pyridinium crosslink and urinary pyridinium peptides larger than 1,000 daltons in molecular weight, of greater than about 5:1.

Where the antibody is for binding native free pyridinoline, the antibody preferably has a ratio of reactivity toward native free pyridinoline and native free deoxypyridinoline of greater than about 5:1, preferably greater than about 20:1, and more preferably greater than about 100:1. Where the antibody is for binding native free deoxypyridinoline, the antibody preferably has a ratio of reactivity toward native free deoxypyridinoline and native free pyridinoline of greater than about 5:1, preferably greater than about 25:1, and more preferably greater than about 100:1.

Where the antibody is for binding both native free pyridinoline and native free deoxypyridinoline, the antibody preferably has a ratio of reactivity toward native free pyridinoline and native free deoxypyridinoline of between about 2:1 and 1:2.

The antibody reagent of the invention preferably has a binding affinity constant for the selected pyridinium species (N-Pyd, N-Dpd, or both) of greater than about $5 \times 10^7$/molar.

A. Immunogen

The immunogen used in producing the antibody reagent is Dpd or Pyd conjugated to a carrier molecule, typically a carrier protein such as keyhole limpet hemocyanin (KLH).

The Pyd can be native Pyd (N-Pyd) or hydrolyzed Pyd (H-Pyd). Likewise, the Dpd can be native Dpd (N-Dpd) or hydrolyzed Dpd (H-Dpd). For obtaining N-Dpd or N-Pyd, gross separation of N-Dpd or N-Pyd from other pyridinium compounds in urine can be achieved by fractionation of urine, as described in Example 2. Briefly, a concentrate of urine is applied to a Sephadex G-10 column, and the total pyridinium-containing fractions are eluted. The eluate is then applied to a column of phosphocellulose equilibrated with sodium citrate, and eluted with salt, yielding free crosslinks in a single peak. As the sample is not subjected to hydrolysis conditions, the peak contains not only the N-Dpd and N-Pyd forms ("free crosslinks"), but also glyco-Pyd, including Gal-Pyd and Glc-Gal-Pyd as described above. Further purification is then conveniently conducted by standard methods, for example, using ion exchange on sulfonated polystyrene beads, or HPLC. Typical protocols for this separation are found, for example, in Black, et al., 1988, Seibel, et al., 1989, and detailed in Example 2.

Alternatively, hydrolyzed Pyd or Dpd can be produced by acid hydrolysis of pyridinium crosslinks in bone collagen or urine, purified as described in Black et al., 1988, for example.

Coupling of Pyd or Dpd to a carrier protein is by standard coupling methods, typically using a bifunctional coupling agent which forms, at one coupling end, an amide linkage to one of the free carboxyl groups of Pyd or Dpd, and at the other coupling end an amide or ester or disulfide linkage to the carrier protein, according to standard methods.

Alternatively, in a preferred embodiment, the Pyd or Dpd can be directly coupled to the protein, e.g., in the presence of a water-soluble carboxyl activating agent such as EDC (1-(3-dimethylaminopropyl)-3-ethylcarbodiimide), also according to well known methods. The latter approach is illustrated in Example 3, which describes the coupling of Dpd to keyhole limpet hemocyanin (KLH) by EDC activation. General coupling reactions for derivatizing a carrier protein with a peptide antigen are given in Harlow (1988), pp. 77–87, and in Wong (1991).

B. Monoclonal Antibody Reagent

To prepare a monoclonal antibody reagent, the immunogen described above is used to immunize an animal, such as a mouse, from which antigen-specific lymphocytes can be obtained for immortalization. One animal that has been found suitable is the "autoimmune" MRL/MpJ-lpr mouse available from Jackson Laboratory (Bar Harbor, Minn.).

Where an antibody which is specific for N-Pyd is desired, a Pyd-immunogen is typically used. Likewise, where an antibody which is specific for N-Dpd is desired, a Dpd-immunogen is typically used. An antibody which recognizes both Pyd and Dpd may be obtained using a Pyd-immunogen or a Dpd-immunogen.

B.1 N-Pyd Monoclonal Antibody. For producing a monoclonal antibody reagent which is specific for N-Pyd, mice can be immunized using a series of injections of H-Pyd-KLH immunogen, as outlined in Example 4. About 8 weeks after initial immunization, spleen cells are harvested and fused with a P3X63Ag8.653 myeloma cell line. Selection for successful fusion products can be performed in HAT in conditioned S-DMEM medium, according to published methods (see, generally, Harlow, pp. 196–212). Successful fusion products are then screened for immunoreactivity with N-Pyd, using a competitive immunoassay format similar to that described in Example 8. Cell lines which show high affinity binding to N-Pyd are subcloned by limiting dilution and further screened for production of antibodies with high binding affinity for N-Pyd. One subcloned cell line obtained by the procedure above and which gave high antibody affinity for N-Pyd is designated herein as Mab-XXV-3G6-3B11-1A10. Samples of this cell line have been deposited with the American Type Culture Collection, 12301 Parklawn Dr., Rockville Md. 20852), and have been assigned ATCC No. HB11089.

To produce the antibody reagent, the hybridoma cell line is grown in a suitable medium (Harlow, pp. 247–270), such as Dulbecco's modified Eagle's medium (DMEM) supplemented as described in the Materials and Methods section below. Monoclonal antibodies ("Mabs") are harvested from the medium and can be concentrated and stored according to published methods (Harlow pp. 271–318).

As noted above, an important feature of the present invention is the specificity of the antibody reagent for N-Dpd and N-Pyd relative to larger molecular weight pyridinium crosslinks in urine. The relative specificity of the antibody reagent for N-Pyd, N-Dpd, and other urinary pyridinium crosslinks can be determined by a competitive binding assays for N-Pyd, as detailed in Example 10.

Briefly, various purified crosslink samples, including N-Pyd and N-Dpd, as well as an amino acid mixture containing the 20 common amino acids in equimolar amounts (150 μM each), are reacted with a limiting amount of the antibody reagent over a solid-phase support having attached N-Pyd under conditions in which the pyridinium crosslinks in the sample compete with the support-bound N-Pyd for binding to the antibody. The extent of binding of antibody to the solid-support provides a measure of the relative reactivities of the sample crosslinks for the antibody reagent.

In accordance with the procedure outlined in Example 10, the levels of binding of N-Pyd, N-Dpd, Pyd-peptides (MW>1,000), and an amino acid mixture (150 μM each of the common 20 amino acids), to monoclonal antibodies from cell line Pyd XXV-3G6-3B11-1A10 were examined. The apparent Pyd concentration of each sample was determined using standard curves established using purified N-Pyd. The percent reactivity of each sample was calculated as a ratio of apparent concentration (measured using the N-Pyd standard curve above) to total Pyd crosslink concentration in the sample determined by HPLC for total H-Pyd (times 100), or to total Dpd-crosslink concentration as determined by HPLC for total H-Dpd (times 100) in the case of the N-Dpd sample. The results are shown in Table 1, where reactivity with N-Pyd has been defined as 100%.

TABLE 1

| Cross-Reactivity of N-Pyd Monoclonal Antibody | |
| --- | --- |
| N-Pyd | 100% |
| N-Dpd | 16% |
| Pyd-Peptide (>1000) | <1% |
| Amino Acid Mixture (150 μM) | <1% |

As seen, the monoclonal antibody reagent is highly selective for N-Pyd relative to N-Dpd, showing a ratio of reactivity toward native free pyridinoline and native deoxypyridinoline that is greater than about 3:1, and in the present case, greater than 5:1. The reagent is also selective for N-Pyd over the pyridinium-peptide forms tested (quantitated for total Pyd content), showing a ratio of reactivity toward pyridinoline peptides larger than 1,000 daltons in molecular weight, of greater than about 100:1. In addition, the reagent shows minimal cross reactivity (<1%) with the amino acid mixture tested.

More generally, the Mab reagent which is specific for N-Pyd has a reactivity toward native free pyridinoline (N-Pyd) and Pyd-peptides (MW>1000), of greater than 5:1, preferably greater than 10:1, more preferably greater than 25:1, and in the present case, greater than 100:1, as measured by the above assay.

B.2 N-Dpd Monoclonal Antibody. For producing a monoclonal antibody reagent which is specific for N-Dpd, the above procedure for obtaining N-Pyd Mabs can be used, except that Dpd-KLH is used as immunogen, and immunoreactivity screening is done with an assay for N-Dpd. One subcloned cell line obtained by this procedure, and which gave high antibody affinity for N-Dpd, is designated herein as Mab-Dpd-II-7B6-1F4-1H11 (see Example 5).

The antibody reagent is prepared from the hybridoma cell line and stored by the same general procedures described above for N-Pyd Mabs.

The relative specificity of the antibody reagent for N-Dpd, N-Pyd, and other urinary pyridinium crosslinks can be determined by the approach described above (section B.1), but using a solid-phase support having attached N-Dpd.

In accordance with the procedure outlined in Example 10, the levels of binding of N-Dpd, N-Pyd, Dpd-peptides (MW>1,000), and an amino acid mixture (150 μM each of the common 20 amino acids), to monoclonal antibodies from cell line Mab-Dpd-II-7B6-1F4-1H11 were examined. The apparent Dpd concentration of each sample was determined using standard curves established using purified N-Dpd. The percent reactivity of each sample was calculated as a ratio of apparent N-Dpd concentration (measured using the N-Dpd standard curve above) to total Dpd-crosslink concentration in the sample determined by HPLC for total H-Dpd (times 100), or to total Pyd-crosslink concentration as determined by HPLC for total H-Pyd (times 100) in the case of the N-Pyd sample. The results are shown in Table 2, where reactivity with N-Dpd has been defined as 100%.

TABLE 2

| Cross-Reactivity of N-Dpd Monoclonal Antibody | |
| --- | --- |
| N-Dpd | 100% |
| N-Pyd | <1% |
| Dpd-Peptide (>1000) | 13% |
| Amino Acid Mixture (150 μM) | <1% |

As seen, the monoclonal antibody reagent is highly selective for N-Dpd relative to N-Pyd, showing a ratio of reactivity toward native free deoxypyridinoline and native free pyridinoline that is greater than about 100:1. The reagent is also selective for N-Dpd over the pyridinium-peptide forms tested (quantitated for Dpd content), showing a ratio of reactivity toward deoxypyridinoline peptides larger than 1,000 daltons in molecular weight, that is greater than about 3:1, and preferably, greater than about 5:1. In addition, the reagent shows minimal cross reactivity (<1%) with the amino acid mixture tested.

More generally, the Mab reagent which is specific for Dpd has a reactivity toward native pyridinoline (N-Dpd) and Dpd-peptides (MW>1000), of greater than about 5:1, preferably greater than 10:1, more preferably greater than 25:1, and in the present case, greater than 100:1, as measured by the above assay.

B.3 Monoclonal Antibodies Which Bind N-Pyd and N-Dpd With Comparable Affinities. For producing a monoclonal antibody reagent which binds N-Pyd and N-Dpd with comparable affinity, the procedures described above for obtaining N-Pyd Mabs and N-Dpd Mabs can be used. The immunogen may be Pyd-KLH or Dpd-KLH, and immunoreactivity screening is done with separate assays for N-Pyd and N-Dpd. One subcloned cell line obtained by the procedure above, using H-Dpd-KLH as immunogen, and which gave high antibody affinity for both N-Dpd and N-Pyd, is designated herein as Mab Pyd/Dpd-V-6H2-2H4-1E4 (see Example 6).

The antibody reagent is prepared from the hybridoma cell line and stored by the same general procedures described above for the N-Pyd Mabs.

The relative specificity of the antibody reagent for N-Dpd, N-Pyd, and other urinary pyridinium crosslinks can be determined by the procedure described above (sections B.1 and B.2). In the present case, for antibodies produced using the Pyd/Dpd-V-6H2-2H4-1E4 cell line, the percent reactivity of each sample was calculated as a ratio of apparent N-Dpd concentration (measured using the N-Dpd standard curve above) to total Dpd crosslink concentration in the sample determined by HPLC for total H-Dpd (times 100), or to total Pyd crosslink concentration determined by HPLC for total H-Pyd in the case of the N-Pyd sample. The results are shown in Table 3, where reactivity with N-Dpd has been defined as 100%.

TABLE 3

| Cross-Reactivity of Pyd/Dpd Monoclonal Antibody | |
|---|---|
| N-Dpd | 100% |
| N-Pyd | 102% |
| Dpd-Peptide (>1000) | 1% |
| Pyd-Peptide (>1000) | 11% |
| Amino Acid Mixture (150 μM) | 5% |

As seen, the monoclonal antibody reagent recognizes N-Dpd and N-Pyd with comparable affinities, with a cross-reactivity ratio close to 1:1. The reagent is also selective for N-Dpd over the pyridinium-peptide forms tested (both Pyd and Dpd peptides), showing a ratio of reactivity toward pyridinium peptides larger than 1,000 daltons in molecular weight, of greater than about 3:1, and in the present case, greater than 9:1. In addition, the reagent shows minimal cross reactivity (5%) with the amino acid mixture tested.

More generally, the Pyd/Dpd-specific Mab reagent has a reactivity toward native free pyridinoline (N-Pyd) and native free deoxypyridinoline (N-Dpd) of between about 2:1 and 1:2.

C. Polyclonal Antibodies

Polyclonal antibody preparation is by conventional techniques, including injection of the immunogen into suitable mammalian subjects, such as rabbits or mice, according to immunological protocols generally known in the art, e.g., Harlow, pp. 93–115. Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to N-Pyd or N-Dpd, according to standard immunoprecipitation methods (Harlow, pp. 423–470). Details of one method for producing polyclonal antibodies in rabbits are given in Example 15.

The binding affinity constant for polyclonal antisera can be determined by known methods (e.g., by Scatchard analysis using an immunoprecipitation or ELISA assay; see Campbell, Segel), and represents an average binding affinity constant value for the antibodies in the antisera which are specific against the selected pyridinium species. Polyclonal antibodies obtained from rabbit VI-8 have a binding constant for N-Pyd of about $1\times10^8$, as determined by Scatchard analysis.

The relative binding specificity of the antibody reagent for the selected pyridinium species and for other pyridinium crosslinks can be determined by a competitive binding assay such as described above and detailed in Example 18. Table 4 shows the relative binding specificities of anti-Pyd antiserum obtained from rabbit VI-8, where reactivity with N-Pyd has been defined as 100%.

TABLE 4

| Cross Reactivity of N-Pyd Polyclonal Antibody | |
|---|---|
| N-Pyd | 100% |
| N-Dpd | <10% |
| Pyd-Peptide (MW > 1000) | <5% |
| Amino Acid Mixture | ~12% |

As seen, the antibody reagent is specific for N-Pyd, showing less than 10% cross-reactivity with N-Dpd, less than 5% cross-reactivity with Pyd-peptides (MW>1000), and moderate (~12%) cross-reactivity with the amino acid mixture. In accordance with one aspect of the invention, the polyclonal antibody reagent has a reactivity toward a selected native free pyridinium species (N-Pyd, N-Pyd, or both) and urinary pyridinium peptides larger than 1,000 daltons in molecular weight, of greater than 3:1, and preferably greater than about 5:1, as measured by the above antigen-competition assay.

B.4 Affinity Chromatography

The antibody reagent of the invention can also be used in an affinity chromatography matrix, in accordance with standard affinity chromatography methods, for binding and collecting native free pyridinium crosslinks derived from collagen tissues, e.g., by passing pooled urine through such a matrix. For isolation of N-Pyd, an antibody reagent which is specific for N-Pyd is used in the matrix. Alternatively, for isolation of both N-Pyd and N-Dpd, an antibody which binds both with comparable affinities is employed. The native free crosslinks obtained can be further purified by methods described in Examples 1 and 2, as necessary.

III. Immunoassay Kit

In another aspect, the invention includes a diagnostic kit for use in assaying collagen degradation levels in a human subject. The kit includes (a) an antibody reagent which is capable of reacting immunospecifically with pyridinium crosslinks selected from the group consisting of native free pyridinoline and native free pyridinoline, where the antibody reagent has a ratio of reactivity toward the selected pyridinium crosslinks and urinary pyridinium peptides larger than 1,000 daltons in molecular weight, of greater than about 5:1, and (b) detection means for detecting the amount of immunocomplex formed by reaction of the antibody reagent with the free pyridinium crosslink(s).

In one general embodiment, the kit includes a solid-phase support having surface-attached binding molecules effective to bind a reporter group in the detection reagent in proportion to the amount of native free pyridinium crosslinks in the sample which are immunoreactive with the antibody reagent.

Figure 1B:
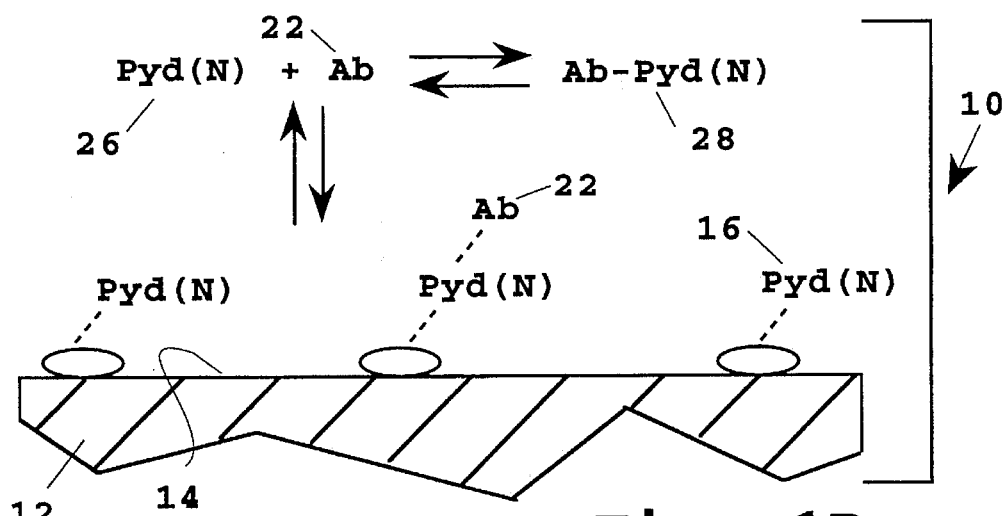
Figure 1C:
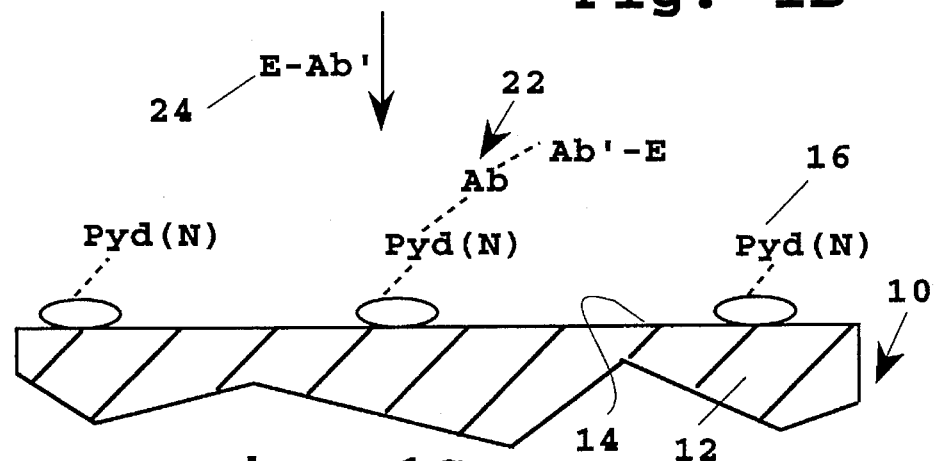

For the purpose of illustration, a specific embodiment of such a kit, for measuring N-Pyd in a sample, is shown at 10 in FIGS. 1A–1C. A solid-phase support 12 in the kit has a surface to which the binding agent can be adsorbed or chemically attached. A variety of glass and polymer resin supports having chemically derivatizable groups, or surfaces effective in protein adsorption are available. In one preferred embodiment, the kit provides 96 assay wells in a microtitre plate, where the well surfaces form the solid-phase support surfaces in the kit.

The binding agent in kit 10 is N-Pyd, indicated by Pyd(N) molecules in the figures, such as at 16. The binding agent is attached to the solid phase, in this case, each of the wells in a 96-well microtitre plate, by first adsorbing an ovalbumin-biotin complex, such as complex 18 in FIG. 1A, to the well surfaces, then attaching an N-Pyd-streptavidin complex, such as complex 20, to the adsorbed biotin. Alternatively, adsorption of an ovalbumin-biotin complex can be omitted, and N-Pyd-streptavidin can be bound directly to the solid support. Methods for forming an N-Pyd coated microtitre plate are detailed in Examples 8 and 9.

The antibody reagent in the kit is indicated at 22 in FIGS. 1B and 1C, and includes, for example, the monoclonal reagent described in the section above. As shown in FIG. 1B, pyridinium crosslinks in a sample, such as the N-Pyd crosslink indicated at 26, competes with surface-bound N-Pyd for binding to the antibody reagent. The immunocomplex formed by reaction of the antibody reagent with sample crosslinks is indicated at 28 in this figure.

The detection reagent in the kit is a reporter-labeled second antibody, indicated at 24 in FIG. 1C, which is effective to bind to antibody reagent which is itself bound to N-Pyd attached to the solid support. Reporter-labeled antibodies, such as enzyme-labeled antibodies, are commercially available or readily constructed (Harlow, pp. 319–358) for a variety of reporter moieties. One preferred enzyme in an enzyme-labeled antibody is alkaline phosphatase, which can react with a p-nitrophenylphosphate substrate to produce a colored product having a strong absorption peak at 405 nm.

The reporter-labeled second antibody is typically an anti-IgG antibody, such as an anti-mouse IgG antibody, where the monoclonal antibody reagent in the kit is obtained from immunized mice. Here, the antibody reagent (which is immunoreactive with N-Pyd as above) is "reporter-labelable", since the antibody reagent can become labeled by reaction with the reporter-labeled second antibody. Other instances of a reporter-labelable antibody reagent include a biotin- or streptavidin-labeled antibody which can be reacted with a reporter-labeled streptavidin or biotin-labeled partner for detection purposes.

In an alternative embodiment, the detection reagent can be the anti-Pyd antibody reagent itself, labeled with a reporter, such as an enzyme.

The detection means in the kit may also include necessary substrates or the like needed for detection of the reporter.

In an alternative embodiment of a kit having a solid-phase support, the binding agent (binding molecule) attached to the support is the antibody reagent described in Section II. The antibody may be attached to the solid support by a variety of known methods, including chemical derivatization or high-affinity binding of the antibody by support-bound protein A or anti-IgG antibody, for example, according to standard methods. In this embodiment, the kit may additionally include a pyridinoline reagent which is effective to compete with N-Pyd in a sample for binding to the antibody reagent on the support. For detection purposes, the pyridinoline reagent may include a reporter-label attached covalently to pyridinoline (i.e., the reagent can be a reporter-labeled pyridinoline). Alternatively, the pyridinoline reagent may be reporter-labelable, in that the pyridinoline reagent can include Pyd conjugated to an agent such as biotin or streptavidin, for example, for recognition by a corresponding reporter-labeled streptavidin or biotin molecule.

In another general embodiment, the kit is designed for a homogenous assay in which sample pyridinoline can be detected directly in solution.

It can be appreciated that the kit of the invention can be adapted to a number of other assay formats, including formats based on radiotracers, coupled enzymes, fluorescence, chemiluminescence, or an EMIT configuration (Gosling), for example, which are known in the art. In another preferred embodiment, the detection means in the kit includes a radioactive reporter group effective to produce a radioactive signal in proportion to the amount of immunocomplex formed by reaction of the antibody reagent with N-Pyd.

While the kit is illustrated above for assay of N-Pyd, it can be appreciated that a similar format can be used where the kit is for measurement of N-Dpd, using an N-Dpd specific antibody reagent, or for measurement of the sum of N-Pyd and N-Dpd, using an antibody reagent which binds N-Pyd and N-Dpd with comparable affinities.

IV. Immunoassay Method

The immunoassay method of the invention provides a method for assaying bone collagen degradation activity in a human subject. The method involves reacting a urine sample from the subject with the antibody reagent described in section II above, forming an immunocomplex between the antibody and native free pyridinoline in the sample, and measuring the amount of immunocomplex formed.

Preferably, as discussed further in Section V, the urine sample is contacted (e.g., via filtration) with a nitrocellulose filter or membrane, prior to reacting the sample with the antibody reagent, to reduce levels of substances in the sample which may interfere with the measurement of N-Pyd.

As indicated in Section III above, the reaction of the urine sample with the antibody reagent may be carried out in a solid-phase format, using a variety of configurations, or in a homogeneous assay format. For illustrative purposes, the immunoassay method is described below with reference to an assay format involving a solid-phase support format like that shown in FIGS. 1A–1C.

In an exemplary embodiment of the method, a known volume, typically 10–100 µl, of the urine sample is added to the N-Pyd-coated solid support, e.g., the wells in a microtitre plate, followed by addition of a known volume, typically 50–200 µl, of antibody reagent, at a known dilution. The mixture on the solid support surface is then incubated, preferably under conditions effective to achieve equilibrium between the antibody, sample pyridinium crosslinks, and surface-bound Pyd. In the method detailed in Example 8, the incubation is overnight at 2°–8° C.

After incubation, the solid support is washed several times to remove antibody not specifically bound to the support, and then incubated with a reporter-labeled anti-IgG antibody or the like, effective to bind specifically to support-bound antibody. Conveniently, for monoclonal antibodies obtained using mice, the reporter-labeled antibody is goat anti-mouse IgG conjugated to alkaline phosphatase. After a short incubation time, the support is again washed to remove non-specifically bound material, and the level of enzyme bound to the support is determined by addition of enzyme substrate, with spectrophotometric determination of converted substrate.

In a typical assay for measuring N-Pyd, N-Pyd standards containing increasing concentrations of N-Pyd are added in duplicate to some of the wells, for purposes of generating an N-Pyd concentration standard curve. Up to 40 samples are then added in duplicate to remaining wells, and the wells are then assayed as above. The standard curve is used for determining the urinary concentration of N-Pyd. The measured concentrations are preferably expressed as a ratio of N-Pyd/creatinine, to normalize the samples for variations in urine concentration and body mass. Urine creatinine concentrations can be assayed by standard methods, such as those based on reaction with alkaline picrate (Cook, 1975).

Assays for measuring N-Dpd in urine are carried out as above, but using an N-Dpd standard curve for determining the concentration of N-Dpd in the sample. Where the assay method measures the sum of N-Pyd and N-Dpd, by means of an antibody reagent that binds N-Pyd and N-Dpd with comparable affinities, it can be appreciated that a standard curve based on one of either N-Pyd or N-Dpd is sufficient in the method, once the relative affinities of the antibody reagent for N-Pyd and N-Dpd have been established.

Example 8 illustrates a typical procedure for assaying urine pyridinium levels in accordance with the invention, using a monoclonal antibody specific for N-Pyd, produced by the Pyd XXV-3G6-3B11-1A10 cells described in Section II.B.1 above. The assay was carried out in two 96 well microtitre plates, with 12 wells in each plate being used for duplicate samples of 6 N-Pyd standards, and 44 wells in each plate being used for 22 duplicate urine samples from post-menopausal women. A standard curve for N-Pyd generated from the six N-Pyd standards was used to calculate, for each unknown sample, the concentration (in nM) of sample pyridinium crosslinks which are immunoreactive with the assay antibody. The data from Table 1 above indicate that the measured pyridinium concentration is due almost entirely to N-Pyd in the sample, with only a minor contribution from N-Dpd.

Figure 2:
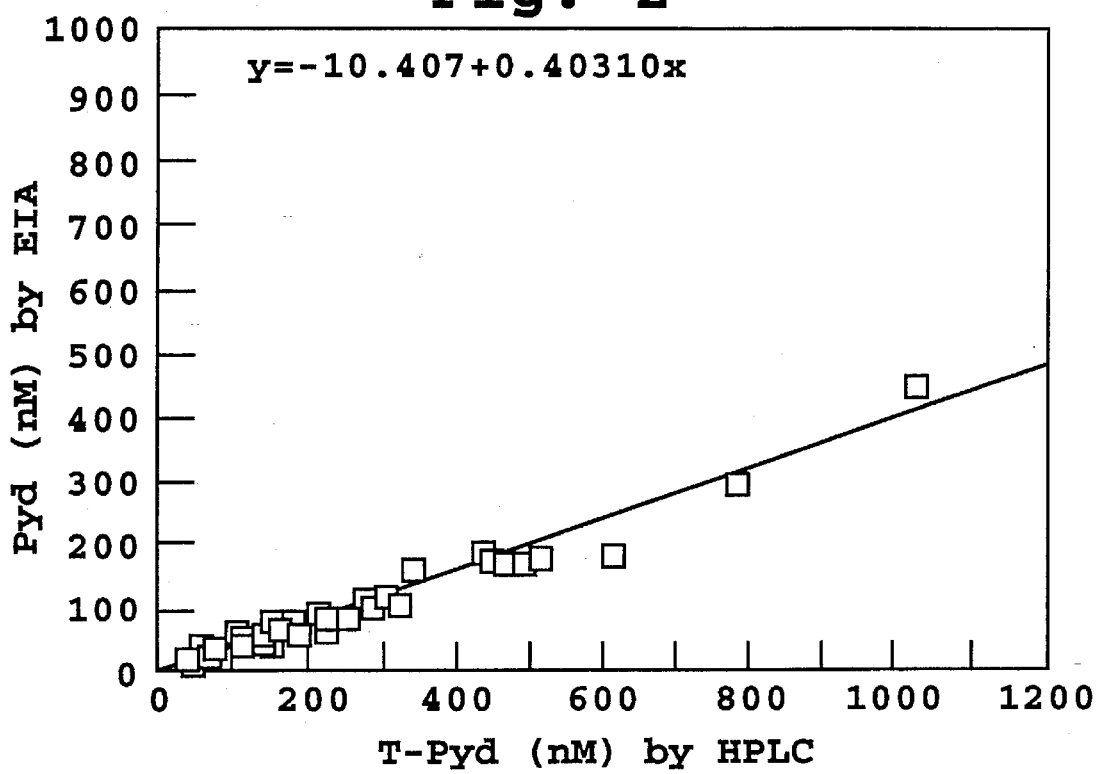
FIG. 2 shows a linear regression plot of native free pyridinoline concentrations measured using a monoclonal antibody reagent of the invention (y-axis), versus total (hydrolyzed) pyridinoline concentration measured by HPLC, in 44 urine samples.

The measured pyridinium crosslink concentrations from the 44 samples were plotted against the total H-Pyd concentrations, measured by HPLC, giving the scatter plot shown in FIG. 2. The best-fit regression line in the figure is given by the equation y=−10.407+0.0.40310x. Thus, the pyridinium crosslink concentration measured in the assay is related to the concentration of total hydrolysed pyridinoline in the sample by linear relationship with a slope of between about 0.3–0.5, and specifically in this set of data, a slope of 0.403. The linear relationship between measured pyridinium crosslink concentration and total H-Pyd, and the high correlation ($r=0.982$) between the two, permits for accurate determination of total Pyd values in the assay from the measure pyridinium crosslink levels.

It will be appreciated how the N-Pyd levels measured in the assay can be used to provide an index to determination of the metabolic status of tissues which generate collagen-derived crosslinks when degradation occurs. As discussed above, a variety of abnormal or pathological bone metabolic conditions are characterized by changes in both N-Pyd and total Pyd in human urine samples. Further, changes in N-Pyd provides a good measure of changes in N-Dpd as well. This latter point is illustrated by the data in Table 5 below, which shows N-Pyd and N-Dpd levels, measured by HPLC from purified N-Pyd and N-Dpd crosslinks in a variety of urine samples.

TABLE 5

| Patient Group | N-Pyd | N-Dpd |
|---|---|---|
| | (nmol/mmol creatinine) | |
| Normal controls | 10.3 ± 1.0 | 3.27 ± 0.57 |
| Osteoporosis | 19.6 ± 2.3 | 5.90 ± 0.68 |
| Paget's Disease | 62.5 ± 11.2 | 19.3 ± 3.83 |
| Hyperparathyroidism | 55.9 ± 14.2 | 16.3 ± 4.81 |
| Rheumatoid arthritis | 38.8 ± 8.36 | 8.92 ± 2.08 |
| Osteoarthritis | 25.8 ± 3.22 | 6.10 ± 0.83 |

These results show dramatically elevated levels of the free crosslinks in patients known to be suffering from diseases characterized by excessive breakdown of connective tissue.

Table 6 shows the proportions of N-Pyd and N-Dpd as a percentage of the respective total crosslink measured after hydrolysis in the different patient groups.

TABLE 6

| Patient Group | % N-Pyd | % N-Dpd |
|---|---|---|
| Normal controls | 43.8 ± 2.5 | 50.1 ± 5.4 |
| Osteoporosis | 41.7 ± 2.0 | 42.7 ± 2.6 |
| Paget's Disease | 46.5 ± 2.4 | 47.4 ± 4.1 |
| Hyperparathyroidism | 48.7 ± 6.8 | 46.2 ± 6.9 |
| Rheumatoid arthritis | 38.1 ± 2.6 | 43.3 ± 1.8 |
| Osteoarthritis | 43.4 ± 3.9 | 47.0 ± 2.2 |

Since, as shown in Table 6, the percentage of N-Pyd (as a percentage of total Pyd) and N-Dpd (as a percentage of total Dpd) is relatively unchanged in patients with abnormal conditions as compared to controls, N-Pyd levels measured in urine reflect the same increase in collagen degradation as do total H-Pyd levels which are measured after hydrolysis of the urine.

V. Pre-Filtration of Urine Sample

In another aspect, the invention includes an assay for quantitating a urinary analyte. In the assay, a urine sample is filtered through a membrane which is effective to remove substance(s) that bind non-specifically to antibodies while allowing the analyte to pass through. The filtered urine sample is reacted with a binding reagent effective to form an antigen-antibody complex with the analyte, under conditions effective to bind the antibody to the solid support in proportion to the amount of analyte in the sample.

The method is based on the discovery that a substance(s) present in variable amounts in urine samples can interfere with the sensitivity, precision, and accuracy of immunoassays. The interfering substance varies from individual to individual, and can also vary in different samples obtained from the same individual.

In accordance with the invention, the interfering substance(s) can be removed by contacting a urine sample with a separation medium (e.g., filter membrane) which is characterized by (i) a binding capacity which is adequate for reducing the level of interfering substance(s) in the sample below a selected threshold amount, and (ii) a low affinity for the analyte of interest, i.e., such that the analyte concentration after sample treatment is essentially the same as before sample treatment. Other desirable features for the separation medium include rapidity of operation and a small retention volume.

Materials which may be used as separation media vary according to the nature of the analyte and include nitrocellulose-based materials, hydrophobic/high protein-binding materials, and charged hydrophilic materials. The configuration of the medium can take a variety of forms, including a strip, bead, cartridge, filter disc, or spin filtration device for example. The efficacy of the separation medium in removing the interfering substance can be evaluated by methods described below.

In one preferred embodiment, illustrated in Example 13–14, the separation medium is configured as a spin filtration device which provides rapid sample through-put. Alternatively, the separation medium may be placed in the sample for a selected time to bind and thereby remove the interfering substance(s) from the sample. Studies carried out in support of the invention suggest that where the separation medium takes the form of a membrane, a small pore size (e.g., less than about 0.45 μm, and preferably less than about 0.1 μm) can increase the binding capacity of the membrane for the interfering substance.

The separation medium and the conditions under which the separation medium is used are tailored to the particular analyte being assayed. In general, it is useful initially to screen candidate separation materials based upon either low affinity for the analyte or high affinity for the interfering substance(s).

Binding of analyte to a particular separation medium can be assessed using one or more standard solutions containing known levels of analyte. Preferably, non-urine solutions are used to avoid the effects of the interfering substance(s). The standard solutions are contacted with (e.g., filtered through) the separation medium, and the analyte is assayed to determine whether any analyte was bound to the separation medium. In another approach, the analyte-content of a urine sample which contains the interfering substance(s) is measured using an analytical method (e.g., HPLC) that is not affected by the interfering substance. The absence of change in the measured analyte level following contact of the sample with the separation medium indicates that further characterization of the medium is warranted.

Capture of the interfering substance(s) by a particular separation medium can be assessed by a number of approaches. For example, the immunoassay which is used for measuring the analyte can be modified to provide an assay that reports the presence of the interfering substance regardless of the presence or absence of the analyte. As illustrated in Example 12, the interfering substance can be detected using an assay that measures the level of binding of reporter-labeled anti-antibody to the solid-support of a microtitre plate in the absence of analyte-specific antibody. A urine sample which causes such non-specific binding of anti-antibody to the solid-support can then be used to assess the effectiveness of a candidate separation medium to reduce or eliminate such non-specific binding caused by the sample.

Once a promising separation material has been identified, the composition and binding capacity of the material can be optimized according to the requirements of the analyte immunoassay.

Typically, the analyte is assayed in a competitive format wherein the urine sample is reacted with an analyte-specific antibody reagent in the presence of a reporter-labeled competitor analyte; the amount of immunocomplex which is formed between antibody reagent and competitor analyte is related inversely to the amount of analyte present in the urine sample. Usually, either the analyte-specific antibody reagent or the reporter-labeled competitor analyte is immobilized on a solid support. Alternatively, a sandwich assay format can be used, where a first antibody for binding analyte is immobilized on a solid support, and a second antibody which is labeled or can be labeled with a reporter (e.g., with an enzyme-labeled anti-antibody) is used to detect analyte which is bound to the first antibody reagent.

The effects of the interfering substance in a representative immunoassay are illustrated by the data shown in Table 7.

These data were obtained using the immunoassay format illustrated in FIG. 1, with N-Pyd as analyte. As detailed in Example 11, aliquots of six urine samples before and after contact with a nitrocellulose filter were assayed, and the apparent level of analyte in each sample was determined by comparison with data obtained from a set of N-Pyd standard solutions.

TABLE 7

| | Quantitation of Pyd | | |
|---|---|---|---|
| Urine ID | Pyd (nM) prefiltration | Pyd (nM) postfiltration | % Increase |
| 2181 | 111 | 205 | 45.8 |
| 2176 | 167 | 201 | 16.9 |
| 2159 | 357 | 592 | 39.7 |
| 2167 | 337 | 365 | 7.7 |
| 2161 | 97 | 137 | 29.1 |
| 2172 | 244 | 362 | 32.6 |

As seen from Table 7, the measured concentration of N-Pyd increased by about 7–45 percent after removal of the interfering substance via nitrocellulose filter disc, indicating wide variability in the extent of interference among samples. Moreover, the analyte concentrations obtained with filtered samples correlated highly with N-Pyd concentrations in the sample, as measured by HPLC, indicating that sample variation due to the interfering substance is largely eliminated by contact with the separation medium.

In the study described in Example 12, the interfering substance is shown to mediate the binding of enzyme-labeled anti-antibody to the solid support in the absence of added anti-analyte antibody. Forty-four urine samples were assayed using the assay format for N-Pyd described in Example 8 in the absence of anti-analyte antibody. Of the 44 samples tested, eight produced optical density readings greater than 0.02 absorbance units, indicating the presence of a substance or substances mediating direct, non-Pyd-specific binding of the enzyme-labeled antibody to the solid support. This non-analyte-specific binding of antibody to the solid support is also observed with other reporter-labeled anti-antibodies, e.g., with rabbit anti-mouse antibodies.

Table 8 shows optical density measurements which were obtained with the 8 problematic urine samples from Example 12, before and after passage of the samples through a nitrocellulose membrane in a spin-filter device (Example 13). The table shows that without prior filtration, the urine samples tested gave rise to optical density readings ranging from 0.36 to 0.101 absorbance units. However, when the urine samples were spin-filtered through a nitrocellulose membrane, the optical density readings were decreased to less than 0.02 absorbance units for all of the samples. Thus, the nitrocellulose membrane is effective to remove the interfering substance such that non-specific binding of anti-antibody to the solid support is substantially reduced.

TABLE 8

| Urine ID | OD (pre-filtration) | OD (post-filtration) |
|---|---|---|
| 1333 | 0.036 | <0.02 |
| 1335 | 0.089 | <0.02 |
| 1337 | 0.101 | <0.02 |
| 1342 | 0.062 | <0.02 |
| 1344 | 0.043 | <0.02 |
| MN36 | 0.041 | <0.02 |
| MN73 | 0.058 | <0.02 |
| 2153 | 0.049 | <0.02 |

It should be appreciated that the occurrence of such non-specific binding is independent of the particular analyte being assayed. Therefore, filtration of a urine sample to remove interfering substance(s), in accordance with the invention can be used in immunoassays for a large variety of analytes.

Tables 9 and 10 illustrate the comparable efficacies of three separation media that have been found useful in removing the interfering substance(s) from urine samples (Example 14). Table 9 shows optical density readings (OD) obtained with 16 urine samples before and after filtration. As can be seen, the optical density readings for the samples prior to filtration ranged from 0.0 to 0.905 absorbance units (second column). However, spin-filtration of the samples through Immobilon-CD (CD) and Immobilon-SPQ (SPQ) filters reduced the optical density readings of the samples to zero, similar to the results obtained with nitrocellulose (NC) (see columns 3–5).

TABLE 9

| sample | OD (pre-filter) | OD (NC) | OD (PSQ) | OD (CD) |
|---|---|---|---|---|
| 1 | 0.092 | 0.001 | −0.002 | −0.003 |
| 2 | 0.027 | −0.008 | 0.001 | 0.011 |
| 3 | 0.012 | −0.001 | −0.003 | 0.003 |
| 4 | 0.210 | −0.005 | −0.002 | 0.002 |
| 5 | 0.066 | −0.003 | 0.000 | −0.001 |
| 6 | 0.010 | −0.003 | 0.000 | 0.001 |
| 7 | 0.062 | −0.003 | 0.000 | −0.004 |
| 8 | 0.034 | −0.005 | −0.003 | −0.006 |
| 9 | 0.296 | −0.002 | −0.003 | −0.005 |
| 10 | 0.905 | 0.002 | 0.003 | 0.005 |
| 11 | 0.018 | 0.002 | −0.003 | 0.004 |
| 12 | 0.045 | 0.006 | 0.000 | 0.011 |
| 13 | 0.008 | 0.004 | 0.001 | 0.004 |
| 14 | 0.034 | −0.002 | 0.002 | 0.003 |
| 15 | 0.000 | −0.004 | 0.000 | −0.002 |
| 16 | 0.081 | 0.002 | −0.004 | −0.004 |

TABLE 10

| Sample | Pyd (nM) NC | Pyd (nM) PSQ | Pyd (nM) CD |
|---|---|---|---|
| 1 | 540.6 | 563.6 | 600.7 |
| 2 | 735.9 | 710.7 | 693.5 |
| 3 | 72.6 | 81.1 | 78.5 |
| 4 | 124.1 | 124.1 | 117.6 |
| 5 | 247.2 | 245.1 | 234.9 |
| 6 | 1047.0 | 1123.0 | 1049.0 |
| 7 | 183.1 | 176.6 | 180.4 |
| 8 | 645.2 | 649.4 | 618.0 |
| 9 | 195.8 | 201.2 | 198.0 |
| 10 | 904.8 | 945.6 | 711.5 |
| 11 | 148.8 | 161.1 | 152.9 |
| 12 | 299.2 | 314.8 | 311.1 |
| 13 | 143.3 | 159.8 | 144.9 |
| 14 | 870.1 | 927.3 | 807.8 |
| 15 | 550.6 | 598.6 | 508.1 |
| 16 | 331.4 | 345.5 | 344.1 |

Table 10 shows that the levels of N-Pyd measured following filtration of the samples through the nitrocellulose (NC), Immobilon-CD (CD), and Immobilon-SPQ (SPQ) membranes were in excellent agreement with one another. Thus, all three media are suitable for removing the interfering substance in accordance with the invention.

VI. Applications

As noted above, the pyridinium crosslink content of collagen-containing tissues varies according to tissue type. Pyd crosslinks are found in cartilage, bone, intervertebral discs, ligaments, and the aorta. Dpd crosslinks are generally less prevalent than Pyd crosslinks and are found in bone, dentine, ligaments, and the aorta. The proportion of Dpd in tissue pyridinium crosslinks appears to be highest in bone, which has a Pyd:Dpd ratio of between about 3:1 and 4:1.

Conditions which are characterized by increased urinary Dpd (and Pyd) levels, and thus are accompanied by elevated rates of bone degradation, include osteoporosis, Paget's disease, hypothyroidism, and osteoarthritis, for example. Other conditions involving increased Pyd and Dpd levels include various forms of metastatic cancer which alter bone metabolism or become established in bone tissue.

The present invention is based in part on the discovery that elevated urinary levels of N-Pyd and N-Dpd are reliable indicators of increased collagen degradation activity in humans. Measurement of an elevated level of N-Pyd or of both N-Pyd and N-Dpd serves as a general indicator of increased collagen degradation. Measurement of urinary N-Dpd via a Dpd-specific antibody in accordance with the invention serves as a relatively specific marker for elevated degradation of bone. The invention is also useful in monitoring antiresorptive therapies associated with management of conditions described above.

In addition, where an assay for N-Pyd is used in combination with an assay for N-Dpd, the invention is useful for distinguishing conditions involving the breakdown of collagen-containing tissues in which the proportion of Dpd crosslinks is substantially less (relative to Pyd crosslinks) than the proportion found in bone. In rheumatoid arthritis, for example, which appears to involve breakdown of connective tissues relatively low in Dpd crosslinks, the ratio of urinary N-Pyd to N-Dpd is elevated compared to the ratio observed with increased bone degradation alone.

Figure 3:
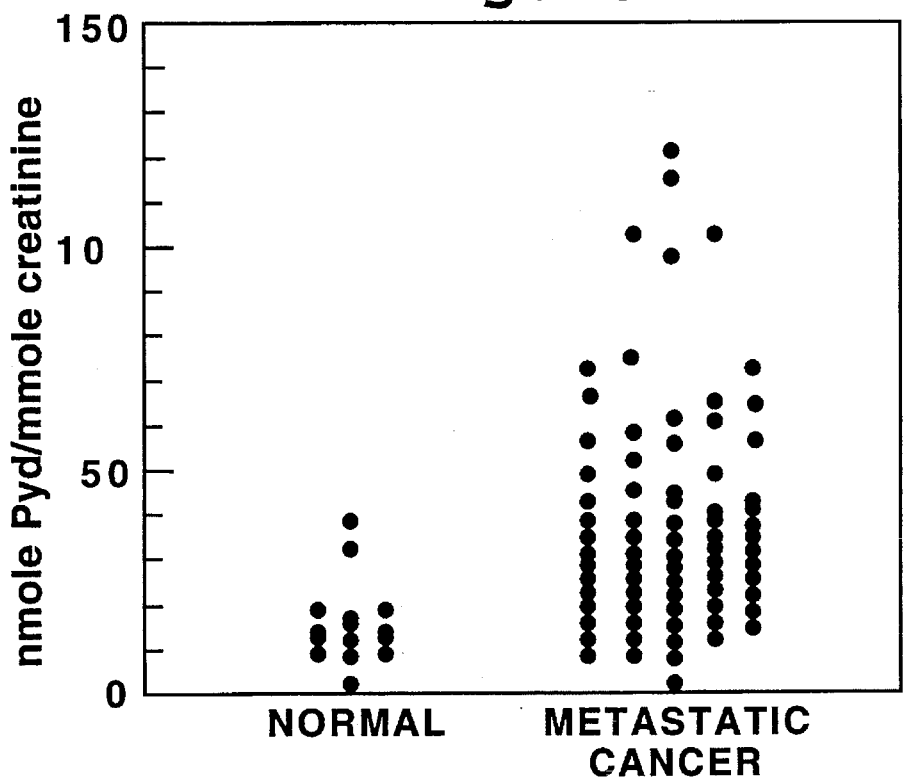
FIG. 3 shows native free pyridinoline levels in normal patients compared with those in metastatic cancer patients, as measured using an assay method in accordance with the invention.

FIG. 3 illustrates use of a Pyd-specific antibody reagent in accordance with the invention, for detecting elevated N-Pyd levels in urine samples from metastic cancer patients. The column of points shown on the left of the figure are levels of N-Pyd (expressed as Pyd/creatinine ratios) measured in a group of healthy subjects. The column of points on the right of the figure are N-Pyd levels measured in patients diagnosed with metastatic cancer. The data reveal patients who have elevated N-Pyd levels, indicating likely bone involvement in their oncological conditions.

Figure 4:
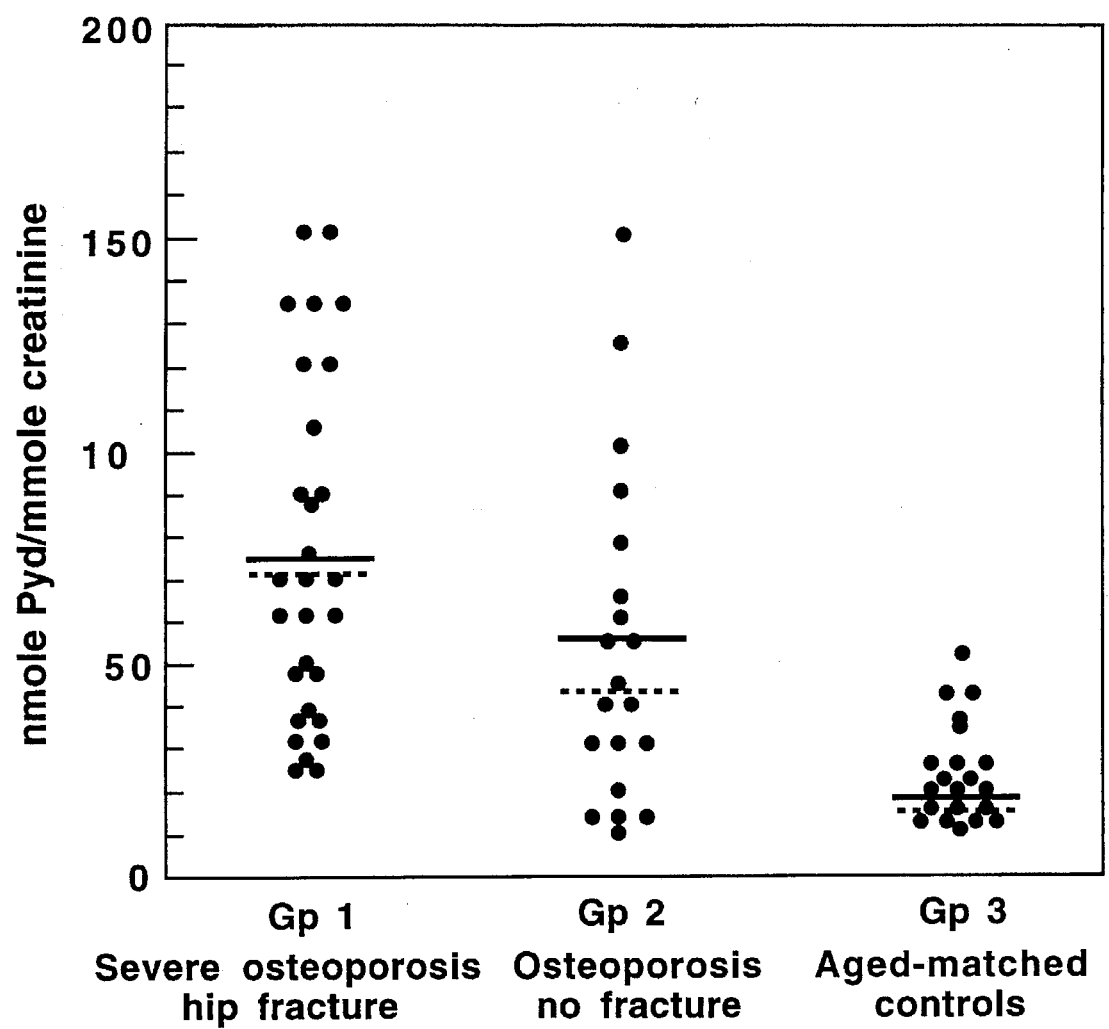
FIG. 4 shows native free pyridinoline levels in patients diagnosed with severe osteoporosis and hip fracture (group 1), osteoporosis in the absence of hip fracture (group 2), and in age-matched control patients, as measured using an assay method in accordance with the invention.

FIG. 4 illustrates use of a Pyd-specific monoclonal antibody reagent for detecting elevated N-Pyd levels in urine samples from osteoporosis patients. The column of points on the right of the figure (group 3) are N-Pyd levels (expressed as Pyd/creatinine ratios) measured in a group of 27 control subjects (age 70–90 years). The middle column of points are N-Pyd levels measured in 20 patients (aged 71–99 years) with overt or suspected osteoporosis (group 2). The column of point on the left (group 1) are N-Pyd levels measured in 30 patients with femoral neck fractures associated with severe osteoporosis. The data show elevated levels of urinary N-Pyd in both osteoporosis patient groups (2 and 3) as compared to the age-matched control group (group 1).

Figure 5:
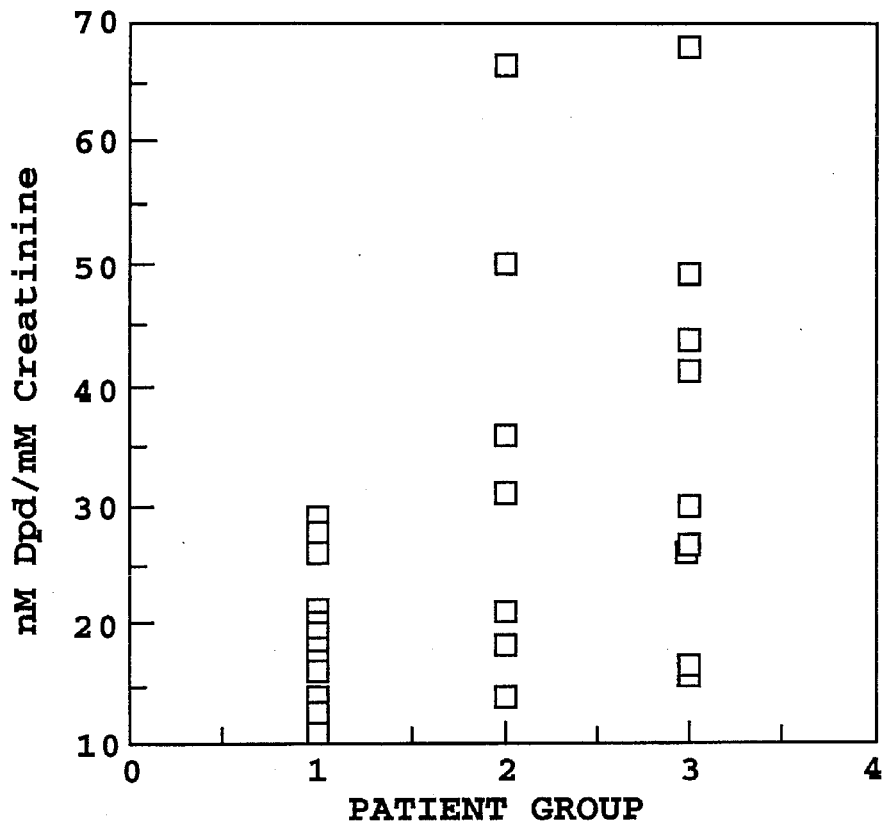
FIG. 5 shows native free deoxypyridinoline levels in normal patients (group 1), patients with metabolic bone disease conditions (group 2), and oncology patients (group 3), as measured using an assay method in accordance with the invention.

Use of a Dpd-specific monoclonal antibody in accordance with the invention, for detecting elevated levels of urinary Dpd, is illustrated in FIG. 5. The points in the left-hand column in the figure are measured Dpd levels (expressed as Dpd/creatinine ratios) for a group of healthy patients. The points in the center column in the figure are the measured Dpd levels from a patient population which includes patients with diagnosed bone metabolism disorders. The right-hand column of points in the figure are measured Dpd levels for a group of oncology patients. The test identifies those patients with elevated Dpd levels, i.e., those patients whose oncological condition likely includes bone involvement.

Figure 6:
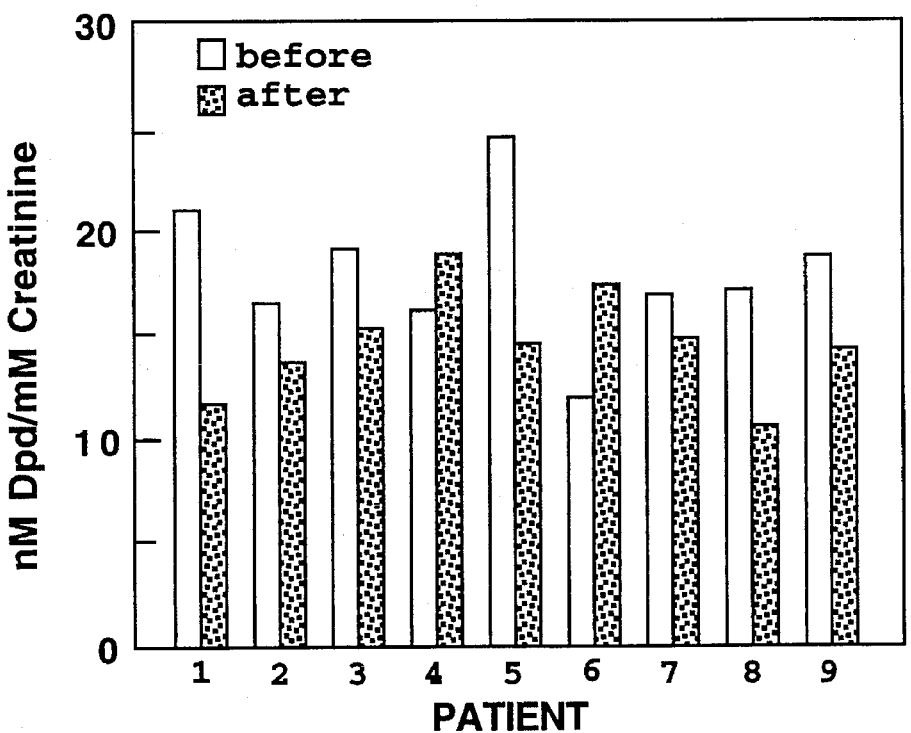
FIG. 6 shows native free deoxypyridinoline levels in osteoporosis patients before and after 1 year of estrogen treatment, as measured using an assay method in accordance with the invention.

FIG. 6 illustrates the use of a Dpd-specific monoclonal antibody of the invention for monitoring estrogen therapy in women under treatment for osteoporosis. In this study, Dpd levels were measured prior to therapy (solid bars in the figure) and after 1 year of estrogen therapy (shaded bars). In seven of the patients, a measurable drop in Dpd levels was observed with therapy, indicating that the therapy is producing the desired reduction in bone resorption. The results in the latter two cases, where Dpd levels have increased with therapy, may indicate that alternative treatment should be considered.

From the foregoing, it can be appreciated how the objects of the invention are met. The native free crosslink assay can be used with a non-hydrolyzed urine sample, thereby avoiding the need for a preliminary acid hydrolysis step. The assay utilizes an antibody reagent, and can thus be adapted to a number of convenient and rapid assay formats known in the art. Moreover, by providing an assessment of the level of native free Pyd, Dpd, or both, in a urine sample, the invention can be used to monitor a variety of collagen-related pathology states.

The following examples illustrate methods of producing antibody reagents and assay methods, in accordance with the invention. The examples are intended to illustrate, but in no way limit, the scope of the invention.

EXAMPLES

Materials and Methods

Reagents for Monoclonal Antibodies Female autoimmune MRL/MpJ-lpr mice were purchased from the Jackson Laboratory, Bar Harbor, Me.

Mouse non-secreting P3X63Ag8.653 myeloma cells, and mouse monocyte-macrophage cell lines P388D1(IL-1) and J774A.1 were purchased from American Type Culture Collection (ATCC), Rockville, Md.

Adjuvant Ribi and Ribi(CWS) were purchased from RIBI Immunochem Research, Inc., Hamilton, Mont. 50% PEG 1500 (polyethylene glycol 1500, 50% (w:v) in water) was purchased from Boehringer Mannheim, Indianapolis, Ind. HAT and HT were purchased from Sigma Chemical Company, St. Louis, Mo.

Dulbecco's Modified Eagle Medium (DMEM), NCTC-109, and gentamicin were purchased from Gibco, Grand Island, N.Y. Fetal clone bovine serum was from Hyclone Laboratories, Inc., Logan, Utah. Oxaloacetic acid and insulin were from Sigma Chemical Company. S-DMEM was formulated as follows, where the percentages indicate final volume percentages in the final medium: DMEM (80%), NCTC-109 (10%), fetal clone bovine serum (10%), oxaloacetic acid (1 mM), L-glutamine (2 mM), gentamicin (50 µg/ml) and insulin (10 µg/ml).

For preparation of conditioned media, mouse monocyte cell lines P388D1 (IL-1), or interchangeably, cell line J774A.1, were grown in S-DMEM medium, with a 1:4 split twice a week. Every 3 days, tissue culture supernatants were filtered through a 0.2 micron filter and then supplemented with 4 mM L-glutamine. The resultant concentrated conditioned media were used as 20% supplement for S-DMEM to raise hybridoma cells.

Unless stated otherwise, PBS is defined as a buffer containing 0.01M phosphate and 150 mM NaCl, pH 7.

Example 1

HPLC Measurement of Crosslinks

HPLC analysis for Pyd and Dpd was done essentially as described by Black et al. (1988). Briefly, urine samples were adjusted with butanol and glacial acetic acid to produce a 4:1:1 mixture (butanol:acetic acid:sample, v:v:v) and applied onto CF1 cellulose (Whatman) cartridges, followed by a wash with 4:1:1 butanol:acetic acid:water. Only free crosslinks (and glyco-Pyd) were retained. The free crosslinks were eluted from CF1 cellulose with water. Eluted material was analyzed on a C18 reverse phase column (Rainin, C18-80-200-C3) using a water-acetonitrile (3–17% in 10 minutes) gradient delivered at 1 ml/minute and monitoring fluorescence at 295 nm of excitation, 395 nm of emission. Mobile phase contained 0.1% HFBA.

Total urinary crosslinks were measured by hydrolyzing a urine sample in HCl (6N) at 110° C. for 16 hours, followed by the CF1 pretreatment and HPLC analysis as above. HPLC separation yielded hydrolysed Pyd and Dpd fractions, from which total H-Pyd and total H-Dpd were quantitated.

Example 2

Purification of Crosslinks

Human urine was filtered through 3000 D molecular cut-off filter (Filton Co.) applying 40 psi of back pressure. The filtrate was then lyophilized and reconstituted to 1/20 of the original volume with 0.2M acetic acid.

Concentrated urine was then applied onto a Sephadex G-10 2.6×95 cm column equilibrated with 0.2M acetic acid. Elution from the column material was analyzed for free Pyd and Dpd as described above. The free crosslink-containing fractions were pooled together, adjusted to pH 2.0 and applied onto 1×18 cm cation exchange column (Lacarte Co., UK) equilibrated with 0.1M sodium citrate, pH 4.2.

Glyco-Pyd, N-Pyd and N-Dpd were coeluted thereafter from the column with 0.1M sodium citrate pH 4.2. Collected fractions were analyzed for the presence of crosslinks by HPLC analysis as above. Fractions containing specific crosslinks (glyco-Pyd, Pyd and Dpd) were pooled together and applied onto a preparative 2.5×10 cm reverse phase C18 column (Waters) which was subsequently developed with 2–20% gradient of acetonitrile containing 0.1% HFBA. Separated fractions (N-Pyd and N-Dpd) were collected separately and concentrated by lyophilization. The dry residues were reconstituted in 0.2M acetic acid and stored at 4° C. Purity of the final materials was measured by gravimetric and elemental analysis.

Urinary crosslink-peptides were prepared by exhaustive dialysis of human urine using 1000 D molecular weight cut-off dialysis membranes (Spectra-Por). The total Pyd crosslink and total Dpd crosslink contents of the peptide fractions was determined by hydrolyzing peptide samples with 6N HCl at 110° C. for 16 hours followed by HPLC analysis for total H-Pyd and total H-Dpd.

Preparative amounts of H-Pyd and H-Dpd were obtained from hydrolyzed powdered bovine or sheep bone as described by Black et al. (1988).

Example 3

Preparation of Immunogens

The following procedures illustrates how immunogens can be prepared for obtaining monoclonal or polyclonal antibodies against native free pyridinoline, native free deoxypyridinoline, or both. The procedures in A and B below are described with respect to Pyd-immunogens; Dpd-immunogens are prepared the same way, but using Dpd instead of Pyd.

A. Pyd-BSA Immunogen

To a 3.1 ml solution consisting of 9 mg of bovine serum albumin (BSA) and 3.8 mg of Pyd in 0.1M MES pH 5.0 was added an 0.88 ml aqueous solution containing 88 mg of EDC. The mixture reacted for four hours at room temperature then was exhaustively dialyzed versus phosphate buffered saline pH 7.0 (PBS). UV and fluorescence measurements indicated 5.8 moles of pyridinoline substituted per mole of albumin.

B. Pyd-KLH Immunogen

To a solution of dried H-Pyd (6 mg) in water adjusted to pH 5±0.5 (200 μl) was added 2 ml of a 10 mg/ml solution of keyhole limpet hemocyanin (KLH) in PBS. To the mixture was added 30 mg solid 1-(3-dimethylaminopropyl)-3-ethylcarbodiimide (EDC, Pierce), and ten minutes later, another 30 mg of EDC, and the reaction was allowed to proceed for 4 h at room temperature. The reaction mixture was then exhaustively dialyzed versus PBS, after which the Pyd-KLH immunogen was collected and stored.

Example 4

Preparation of Anti-Pyd Monoclonal Antibodies

A. Immunization protocol

Female 5-week-old autoimmune MRL/MpJ-lpr mice were immunized using the protocol below:

TABLE 11

Immunization Protocol for Pyd Mice

| Immunization | Days from Fusion | Immunogen Injected (μg) | [1]Adjuvant | Inject. Mode |
|---|---|---|---|---|
| 1 | 60 | 100 | Ribi | ip[2] |
| 2 | 46 | 100 | Ribi | ip |
| 3 | 32 | 100 | Ribi | ip |
| 4 | 18 | 100 | Ribi | ip |
| 5 | 4 | 200 | — | iv[3] |

[1]Adjuvant and antigen were suspended in Hank's balanced salt solution
[2]Intraperitoneal
[3]Intravenous On the day of fusion, the immunized mouse was sacrificed by $CO_2$ gas, and the spleen was excised from the mouse and placed in a culture dish containing 5 ml of serum-free DMEM medium preheated to 37° C. Following removal of adipose tissue attached to the spleen, the spleen was washed with 5 ml of serum-free DMEM medium. The spleen was then cut into small pieces which were placed in a cell homogenizer containing 7 ml of serum-free DMEM medium, and the cells were homogenized to form a cell suspension.

B. Fusion Protocol

The following steps were performed at room temperature.

The spleen cell suspension (~2×10⁸ cells in serum-free DMEM medium) and log-phase P3X63Ag8.653 myeloma cells (~7×10⁷ cells in serum-free DMEM medium) were centrifuged independently at 400× g for 10 min. The resultant cell pellets were suspended together in serum-free DMEM medium (10 ml) in a 50 mL centrifuge tube and then centrifuged at 400× g for 10 min. The supernatant was removed completely, and the centrifuge tube was tapped to loosen the cell pellet.

For cell fusion, a solution of 50% PEG 1500 (4 ml) was added dropwise to the tube with gentle mixing by pipette over a 90 second period. Next, serum-free DMEM (4 ml) was added dropwise over 1 min. S-DMEM (40 ml) was then added over 2 min with gentle mixing, after which the mixture was mixed by pipette for an additional 2.5 min. The resultant mixture was centrifuged at 400× g for 10 min. After thorough removal of the supernatant, the cells were suspended in 320 ml of HAT in 20% P388D1-conditioned S-DMEM medium. The cell suspension was plated in 16 96-well tissue culture plates, 200 μl/well, and the plates were then incubated at 37° C. in an atmosphere containing 7% $CO_2$. The cell mixtures were fed at day 3 and day 7 by removing 100 μl/well of old medium and adding 150 μl/well of either HAT medium (day 3) or HT medium (day 7). The wells were ready to screen 7 to 10 days after fusion.

C. Screening Hybridomas for Production of Anti-N-Pyd Monoclonal Antibodies

Successful fusion products were screened for immunoreactivity using the N-Pyd immunoassay format described in Example 8. Cell lines which showed high affinity binding to N-Pyd were subcloned by limiting dilution and further screened for production of antibodies with high binding affinity for N-Pyd. One of the subcloned cell lines which gave high antibody affinity for N-Pyd is designated herein as Mab Pyd-XXV-3G6-3B11-1A10. The specificity of antibodies produced by this cell line is shown in Table 1 above.

Example 5

Preparation of Anti-Dpd Monoclonal Antibodies

Anti-Dpd monoclonal antibodies were prepared by the procedure described in Example 4, using Dpd-KLH immunogen prepared as in Example 3. The mouse immunization procedure was the same as in Example 4, except that Ribi(CWS) was used as adjuvant instead of Ribi, and 75 μg imunogen per mouse was used in the fourth immunization step (18 days from fusion) instead of 100 μg.

Successful fusion products were screened for immunoreactivity using the N-Dpd immunoassay format described in Example 9. Cell lines which showed high affinity binding to N-Dpd were subcloned by limiting dilution and further screened for production of antibodies with high binding affinity for N-Dpd. One of the subcloned cell lines which gave high antibody affinity for N-Dpd is designated herein as Mab Dpd-II-7B6-1F4-1H11. The specificity of antibodies produced by this cell line is shown in Table 2 above.

Example 6

Preparation of Monoclonal Antibodies Specific for Both N-Pyd and N-Dpd

Monoclonal antibodies specific for both N-Pyd and N-Dpd were prepared by the procedure in Example 5, using H-Dpd-KLH (Example 3) as immunogen. Successful fusion products were screened for immunoreactivity using the N-Dpd immunoassay format described in Example 9. Cell lines which showed high affinity binding to N-Dpd were subcloned by limiting dilution and further screened for production of antibodies with high binding affinity for both N-Pyd and N-Dpd. One of the subcloned cell lines which gave high antibody affinity for both N-Pyd and N-Dpd is designated herein as Mab Pyd/Dpd-V-6H2-2H4-1E4. The specificity of antibodies produced by this cell line is shown in Table 3 above.

Example 7

Preparation of H-Pyd-Streptavidin and H-Dpd Streptavidin

Conjugation of H-Pyd to streptavidin was accomplished by coupling a thiolated streptavidin to H-Pyd via the coupling agent, SMCC. Thiolated streptavidin was prepared by reaction with N-succinimidyl-3-(2-pyridylthio)proprionate (SPDP, Pierce) as follows. To a 0.75 ml solution of 5 mg of streptavidin in PBS was added 21 uL of dimethylformamide containing 260 ug of SPDP. The mixture was allowed to react for one hour at room temperature, and then was dialysed against PBS. The SPDP-labeled streptavidin was reduced by the addition of dithiothreitol to a final concentration of 10 mM. After incubation for one hour at room temperature, the thiolated streptavidin was purified on a G-25 column.

To form H-Pyd-streptavidin, a solution containing 180 ug of succinimidyl 4-(N-maleimidomethyl)cyclohexane-1-carboxylate (SMCC, Pierce) in dimethylformamide (4 ul) was added to a solution containing 0.5 mg thiolated streptavidin and 50 ug of H-Pyd in 100 µof PBS. The mixture was allowed to react for 3 hours at room temperature and then was dialysed versus PBS. Spectrophotometric analysis of the resultant Pyd-streptavidin indicated between 1 and 2 equivalents of pyridinoline bound per equivalent of streptavidin.

H-Dpd-streptavidin was prepared by the same procedure except that H-Dpd was used in place of H-Pyd.

Example 8

Immunoassay Using Anti-Pyd Monoclonal Antibody Reagent

A. H-Pyd-Coated Microtitre Plates

Biotin-labeled ovalbumin and H-Pyd-streptavidin (Example 7) were utilized in the microplate coating.

Biotinylation of ovalbumin was carried out by adding 10 mg of biotin-X-2,4-dinitrophenol-X-L-lysine, succinimidyl ester (Molecular Probes) in 400 microliters of dimethylformamide to a 10 ml solution of PBS containing 150 mg of ovalbumin. The mixture was reacted for two hours at room temperature followed by G25 column chromatography. Spectrophotometric analysis indicated two biotins substituted per mole of ovalbumin.

The wells in a 96-well ELISA plate were coated with N-Pyd as follows. To each well was added 150 microliters of biotin-ovalbumin solution at 3.8 ug/ml in PBS, followed by an overnight incubation at 2°–8° C. The wells were washed with PBS and blocked by adding 200 ul of ovalbumin at 1 mg/ml with an overnight incubation at room temperature. The wells were then twice washed with PBS. 150 ul of a solution containing H-Pyd-streptavidin at 100 ug/ml in PBS was added to each well of the biotin-ovalbumin coated microplate. After a one hour incubation at room temperature, the wells were twice washed with PBS. Residual liquid was removed from the wells by drying overnight in a convection oven at 37° C.

B. Assay Protocol

N-Pyd standard solutions and urine samples were tested in duplicate. The standard solutions consisted of 0 nM, 25 nM, 75 nM, 250 nM, 750 nM, and 3000 nMN-Pyd in assay buffer (0.05% NAN3, 0.05% Tween 20, and 0.1% BSA in PBS). Urine samples were filtered through a nitrocellulose membrane by centrifugation (spin filtration) prior to assay.

Using microtitre plates prepared as above, 20 ul/well of the standard solutions were added in duplicate to 12 of the 96 wells in the coated plates, and 20 ul/well of each of 44 urine samples were added in duplicate to wells of two microtitre plates.

100 ul/well of MAb 3G6-3B11-1A10 (1:100,000 dilution) in assay buffer (0.05% NAN3, 0.05% Tween 20, and 0.1% BSA in PBS) were added. The standards or samples and MAb mixtures were incubated at 4° C. overnight. 100 µl/well of goat anti-mouse IgG+M(H+L)-alkaline phosphatase conjugate (Pierce, No. 31330, 1:1000 dilution in assay buffer) were added to the plate and incubated at room temperature for one hour.

To each well was added 100 uL of enzyme substrate solution (2 mg/mL of p-nitrophenylphosphate (Sigma) in 1.0M diethanolamine, pH 9.8, containing 1 mM $MgCl_2$). Following a 30 min incubation at room temperature, 50 µl of 3.0N NaOH was added to each well to stop the enzymatic reaction. The optical density at 405 nm was then measured with a Vmax reader (Molecular Devices Corp.).

The optical density readings (405 nm) from duplicate sample were averaged, and the averaged readings from the N-Pyd standards were used to construct a standard curve of OD reading vs. N-Pyd concentration. From this curve, the free N-Pyd crosslink concentration in each urine sample was determined. Creatinine concentrations were measured using an assay involving alkaline picrate (Cook, 1975).

The same urine samples were quantitated for total Pyd by the HPLC method described in Example 2. Briefly, the urine samples were hydrolysed in HCL (6N) at 110° C. for 16 hours, followed by the CF1 pretreatment and HPLC analysis for total H-Pyd.

FIG. 2 shows a scatter plot of pyridinium crosslinks (in nM) measured by the immunoassay method (y axis) measured vs. total H-Pyd measured by HPLC. The line in the plot is the best-fit linear regression equation which correlates immunoassay values as a function of HPLC total Pyd values.

Example 9

Immunoassay Using Anti-Dpd Monoclonal Antibody Reagent

A. H-Dpd-Coated Microtitre Plate

To each well of a 96-well ELISA plate was added 100 µl of a solution containing H-Dpd-streptavidin (0.5 ug/ml in PBS). After overnight incubation at 4° C., the wells were emptied and then blocked by incubation with ovalbumin (1 mg/ml in PBS, 150 µl/well) for at least 1 h at room temperature or overnight at 4° C. After incubation, the plates were washed 3 times with PBS.

B. Assay Protocol

N-Dpd standard solutions and urine samples were tested in duplicate. The standard solutions consisted of 0 nM, 25 nM, 50 nM, 100 nM, 250 nM, and 500 nM N-Dpd in assay buffer (0.05% NAN3, 0.05% Tween 20, and 0.1% BSA in PBS). Urine samples were filtered through a nitrocellulose membrane by centrifugation (spin filtration) prior to assay.

Following the addition of sample (10 µl/well), 100 ul/well of 7B6-1F4-1H11 monoclonal antibody (1:1600 dilution of tissue culture supernatant into assay buffer, ~10 ng/ml antibody) was added, and the assay plate was incubated at 4° C. overnight. After the plate was washed 3 times with 300 µl/well of wash buffer, 100 µl/well of goat anti-mouse IgG+M(H+L)-alkaline phosphatase conjugate (Pierce, No. 31330) (1:1000 dilution in assay buffer) was added, and the plate was incubated at room temperature for 1 h. The wells were then washed 3 times with wash buffer.

Bound enzyme was assayed as in the preceding Example. The N-Dpd crosslink concentration for each unknown urine sample was determined by quantitation from the standard curve.

Example 10

Binding Selectivity of Monoclonal Antibody Reagents

N-Pyd, N-Dpd, pyridinium-peptides (MW>1000) were isolated from urine samples as described above. Aliquots of the pyridinium preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Dpd in the pyridinium-peptide preparations, were determined by HPLC, as in Example 1. In addition, an amino acid solution containing an equimolar mixture of the 20 common amino acids, 150 µM each in PBS, was prepared.

Aliquots (50 µl) of the native crosslink preparations and the amino acid mixture were added in duplicate to Pyd-coated or DpD-coated microtitre wells, prepared as above, and each well was assayed for pyridinoline or deoxypyridinoline as in Example 8 or 9, as appropriate. The optical density readings (405 nm) from duplicate samples were averaged, and from these values, the apparent N-Pyd or N-Dpd concentration of each sample was determined using a standard curve established with purified N-Pyd or N-Dpd. The percent reactivity of each sample was calculated as a ratio of apparent concentration (using a standard curve; see Examples 8 and 9) to total Pyd crosslink concentration in the sample determined by HPLC for total H-Pyd (times 100), or total H-Dpd in the case of total Dpd crosslink concentration. Results obtained with antibodies having various specificities are given in Tables 1, 2 and 3 above.

Example 11

Nitrocellulose Syringe Filtration

Six urine samples designated 2181, 2176, 2159, 2167, 2161, and 2172 were tested. An aliquot (400 µl) of each sample was syringe-filtered through a 25 mm diameter 0.45 µm pore size nitrocellulose filter (Millipore, Millex-HA, Bedford, Mass.) and the filtrate was collected in a tube. Aliquots (10 µl) of filtered and unfiltered sample material and of N-Pyd standards were added in duplicate to the wells of a 96 well microtitre plate prepared as in Example 8, and the concentration of N-Pyd in each sample was determined as generally described in Example 8, using an N-Pyd-selective polyclonal antibody, and an alkaline phosphatase-labeled goat anti-rabbit antibody. The results are shown in Table 7.

Example 12

Assessment of Non-Specific Binding Mediated by Urine Samples

Urine samples were tested for the presence of interfering materials by the following procedure. Aliquots (10 µl) of buffer, N-Pyd standards, and each of 44 urine samples were placed in duplicate in the wells of two 96-well microtitre plates. The assay procedure described in Example 8 was carried out except that the anti-N-Pyd antibody was replaced with assay buffer or with diluted tissue culture. Wells to which buffer alone, diluted tissue culture, or N-Pyd standard had been added afforded optical density readings of less than 0.010. Of the 44 urine samples tested, 8 produced readings which were greater than 0.02 absorbance units (Table 8).

Example 13

Removal of Interfering Substance by Spin Filtration

The 8 urine samples from Example 12 which produced optical density readings greater than 0.02 were subjected to a spin filtration step as follows. An aliquot (200 µl) of each sample was placed in a nitrocellulose filter unit suspended inside a 1.5 mL microfuge tube (the filter unit and microfuge together are referred to as "filter assembly"). The filter unit (constructed by Lida Manufacturing Corp, Kenosha, Wis.) included a polypropylene cylindrical housing (40 mm length×10 mm outer diameter) containing at its lower end a double layer of nitrocellulose membranes (0.1 µm pore size) and a non-woven polyethylene support. The effective filtration cross-section of the nitrocellulose membranes was 0.2 cm². The sample-containing filter assemblies were then centrifuged at 1500× g for 2 minutes to pass the samples completely through the filters. The samples were then processed as described in Example 8, but with assay buffer used in place of anti-Pyd antibody. The measured optical densities of all eight filtered samples were less than 0.02 (Table 8).

Example 14

Comparison of Spin Filters

Aliquots (200 µl) of 16 urine samples were centrifuged in spin-filter assemblies containing one of the following membrane materials: nitrocellose (Lida Manuf. Corp, Kenosha, Wis.), Immobilon-CD (Millipore Corp., Bedford, Mass. catalog no. ICDM-00000), and Immobilon-PSQ (Millipore, catalog no. ISEQ-00000). The nitrocellulose-containing filter assembly was configured as described in Example 13. The Immobilon-containing filter assemblies were configured similarly to those which contained nitrocellulose, except that the Immobilon membranes were single- rather than double-layered, with a 0.1 µm pore size.

Aliquots (10 µl) of filtered and unfiltered urine samples were added in duplicate to the wells of a 96 well microtitre plate prepared as in Example 8. The assay procedure described in Example 8 was carried out except that the anti-N-Pyd antibody was replaced with assay buffer. The optical density readings produced by the urine samples are shown in Table 9 (all values were corrected by subtracting the absorbance of buffer alone). N-Pyd concentrations measured in the same samples using a calibration curve established with N-Pyd standards are shown in Table 10.

Example 15

Preparation of Anti-Pyridinoline Antiserum

New Zealand white rabbits (a total of 59) for immunization were divided into eight groups according to immunization protocol, as indicated below in Table 12. The immunization dose was 200 µg of Pyd-BSA (Example 3A), low-hapten Pyd-BSA immunogen (prepared as in Example 3A for Pyd-BSA, but with a lower Pyd:BSA stoichiometry), or Pyd-KLH (Example 3B), in 1.0 ml PBS mixed with 1.0 ml of Ribi adjuvant (Ribi ImmunoChemical Research, Inc.). Initial immunization was by subcutaneous injections at multiple sites, and subsequent booster immunizations were given at three week intervals intramuscularly. Antiserum was collected 10 days after each immunization.

TABLE 12

| Group | # Rabbits | Rabbits Kept | Carrier |
|-------|-----------|--------------|---------|
| I | 4 | 1 | BSA |
| II | 10 | 0 | BSA |
| III | 10 | 2 | BSA |
| IV | 5 | 1 | BSA |
| V | 5 | 2 | BSA |
| VI | 10 | 1 | KLH |
| VII | 5 | 0 | Low Hapten BSA |
| VIII | 10 | 1 | BSA |
| Total | 59 | 8 | |

Upon collection, each antiserum was tested for Pyd binding affinity using an assay format similar to that described in Example 17. In brief, binding of anti-Pyd antibodies from the serum to Pyd immobilized on a solid support was detected using an alkaline phosphatase-labeled goat anti-rabbit IgG antibody reagent.

Immunized animals were kept if their antisera satisfied the following criteria, defined further in the following paragraph: AA<20%, Pyd-peptide<10%, titer>5000, and a 0 to 25 nM Pyd signal separation of >10% of total modulated signal.

Profiles of the most strongly reactive antisera are shown in Table 13 below, as measured using the assay format described in Example 17. The first column indicates the immunization program from which the rabbit antiserum came. The second column indicates the bleeds which were used for analysis. The column marked "titer" indicates the average dilution of each antiserum necessary to achieve an optical density reading of 1.2 to 1.6 with a Pyd-negative sample (no Pyd present) in the immunoassay. The column marked "AA" shows the average cross-reactivity of each antiserum with the amino acid mixture described in Example 18. The column marked "Pyd-pep >1000 MW" shows the average cross-reactivity of each antiserum with Pyd-peptides (>1000 MW). The last column shows the separation between signals for 0 and 25 nM Pyd samples as a fraction of the total modulated signal.

TABLE 13

| Rabbit # | Bleeds | Titer | AA | Pyd-pep. >1000 MW | Sens. 25 nM |
|---|---|---|---|---|---|
| I-3 | 21–28 | 200K[1] | 2% | 4.6% | 18% |
| III-3 | 11–18 | 20K | 16% | 8.3% | 37% |
| III-5 | 11–18 | 52K | 1% | 8.1% | 13% |
| IV-4 | 4–14 | 84K | 4% | 4.9% | 10% |
| V-3 | 4–14 | 22K | 18% | 4.0% | 15% |
| V-4 | 11–14 | 9700 | 15% | 5.2% | 29% |
| VI-8 | 2–11 | 30K | 10% | 0.6% | 61% |
| VIII-4 | 3–10 | 34K | ~0% | 3.4% | 11% |

[1]K = ×1000.

As can be seen, rabbits III-3, V-4, and VI-8 showed significant modulation of signal from 0 to 25 nM N-Pyd. The serum with highest activity (VI-8) was selected for use in the N-Pyd assays described herein.

Example 16

Preparation of N-Pyd-Coated Microplates

Biotin-labeled porcine ovalbumin and a streptavidin-Pyd conjugate were utilized in the microplate coating. Biotinylation of the ovalbumin was carried out by adding 10 mg of biotin-X-2,4-dinitrophenol-X-L-lysine, succinimidyl ester (Molecular Probes) in 400 microliters of dimethylformamide to a 10 ml solution of PBS containing 150 mg of ovalbumin. The mixture was allowed to react for two hours at room temperature, followed by G25 column chromatography. Spectrophotometric analysis indicated two biotins substituted per mole of ovalbumin.

Conjugation of N-Pyd to streptavidin was accomplished by coupling a thiolated streptavidin to N-Pyd via the coupling agent, SMCC. Thiolated streptavidin was prepared by reaction with N-succinimidyl-3-(2-pyridylthio)proprionate (SPDP, Pierce) as follows. To a 0.75 ml solution of 5 mg of streptavidin in PBS was added 21 uL of dimethylformamide containing 260 ug of SPDP. The mixture was allowed to react for one hour at room temperature, and then was dialysed against PBS. The SPDP-labeled streptavidin was reduced by the addition of dithiothreitol to a final concentration of 10 mM. After incubation for one hour at room temperature, the thiolated streptavidin was purified on a G-25 column.

To form N-Pyd-streptavidin, a solution containing 180 ug of succinimidyl 4-(N-maleimidomethyl)cyclohexane-1-carboxylate (SMCC, Pierce) in dimethylformamide (4 ul) was added to a solution containing 0.5 mg thiolated streptavidin and 50 ug of N-Pyd in 100 µl of PBS. The mixture was allowed to react for 3 hours at room temperature and then was dialysed versus PBS. Spectrophotometric analysis of the resultant Pyd-streptavidin indicated between 1 and 6 equivalents of pyridinoline bound per equivalent of streptavidin.

Each of the wells in a 96-well ELISA plate were coated with with N-Pyd as follows. To each well was added 150 microliters of biotin-ovalbumin solution at 3.8 ug/ml in PBS, followed by an overnight incubation at 2°–8° C. The microplates were washed with PBS and blocked by adding 200 ul of ovalbumin at 1 mg/ml with an overnight incubation at room temperature. The microplates were then twice washed with PBS. The streptavidin-Pyd conjugate is immobilized via the streptavidin mediated binding to biotin. 150 ul of a solution containing streptavidin-Pyd at 100 ng/ml in PBS was added to each well of the biotin-ovalbumin coated microplate. After a one hour incubation at room temperature, the plates are twice washed with PBS, and then with 200 µL of 10% sucrose in 100 mM PBS for 2 hours. Residual liquid was removed from the microplate by drying overnight in a convection oven at 37° C.

Example 17

Immunoassay for Pyd Using Polyclonal Antibody Reagent

The following immunoassay is performed using rabbit polyclonal antibody VI-8 characterized in Tables 4 and 13 above, and the N-Pyd-coated microtiter plate described in Example 16.

N-Pyd standard solutions and urine samples are tested in duplicate. The standard solutions consisted of 0 nM, 0.2 nM, 0.6 nM, 2.0 nM, 6.0 nM, and 24 nM N-Pyd in assay buffer (0.05% NAN3, 0.05% Tween 20, and 0.1% BSA in 100 mM sodium phosphate containing 150 mM NaCl, pH 7). Samples are filtered through a Centricon-30 filter device (Amicon, Mass.) prior to assay.

Following the addition of sample or standard (25 µl/well), 125 ul/well of VI-8 antiserum diluted 20,000-fold in assay buffer is added, and the assay plate is incubated at 4° C. overnight. After the plate is washed 3 times with 300 µl/well of wash buffer, 150 µl/well of goat anti-rabbit IgG-alkaline phosphatase conjugate (1:1000 dilution in assay buffer) is added, and the plate is incubated at room temperature for 1 h. The wells are then washed 3 times with wash buffer.

To each well is added 150 uL of enzyme substrate solution (2 mg/mL of p-nitrophenylphosphate (Sigma) in 1.0M diethanolamine, pH 9.8, containing 1 mM MgCl$_2$). Following a 1 hour incubation at room temperature, 50 µl of 3.0N NaOH is added to each well to stop the enzymatic reaction. The optical density at 405 nm is measured with a Vmax reader (Molecular Devices Corp.).

The optical density readings (405 nm) from duplicate samples are averaged, and the averaged readings from the N-Pyd standards are used to construct a standard curve of OD reading vs. N-Pyd concentration. From this curve, the free N-Pyd crosslink concentration in each sample is determined.

Example 18

Binding Selectively of Polyclonal Antibody Reagent

N-Pyd, N-Dpd, and pyridinium-peptides (MW>1000) were isolated from urine samples as described above. Aliquots of the pyridinium preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Pyd in the pyridinium-peptide preparation, were determined by HPLC, as in Example 1. In addition, an amino acid solution containing an equimolar mixture of the 20 common amino acids, 150 µM each in PBS, was prepared.

Aliquots (50 µl) of the native crosslink preparations and the amino acid mixture were added in duplicate to Pyd-coated microtitre wells, and each well was assayed for pyridinoline as in Example 17. The optical density readings (405 nm) from duplicate samples were averaged, and from these values, the apparent N-Pyd concentration of each sample was determined using a standard curve established with purified N-Pyd. The percent reactivity of each sample was calculated as a ratio of apparent concentration (measured using the N-Pyd standard curve above) to total Pyd crosslink concentration in the sample determined by HPLC for total H-Pyd (times 100). The relative reactivity determined for purified N-Pyd was arbitrarily set at 100%, and the reactivities of the other crosslink preparations (and the amino acid mixture) were expressed as a percentage of 100. Results are shown in Tables 4 and 13.

Although the invention has been described with respect to particular embodiments, it will be appreciated that various changes and modifications can be made without departing from the invention.

Although the invention has been described with respect to particular embodiments, it will be appreciated that various changes and modifications can be made without departing from the invention.

It is claimed:

1. A method of screening or monitoring bone collagen degradation activity in a human subject, comprising reacting a non-hydrolyzed human urine sample with an antibody which is capable of reacting immunospecifically with pyridinium crosslinks selected from the group consisting of native free pyridinoline, native free deoxypyridinoline, or both, said antibody having been produced by immunizing an animal with hydrolyzed pyridinoline or hydrolyzed deoxypyridinoline, said antibody having a ratio of reactivity toward said selected pyridinium crosslinks and urinary pyridinium peptides larger than 1,000 daltons in molecular weight, of greater than about 5:1, by said reacting, forming an immunocomplex between the antibody and such selected pyridinium crosslinks present in the sample, and from the amount of immunocomplex formed, determining the level of such selected pyridinium crosslinks in the sample, whereby a determined level which is above that characteristic of normal subjects indicates the presence of an elevated rate of bone collagen degradation in the subject.

2. The method of claim 1, wherein said antibody has a ratio of reactivity toward native free pyridinoline and native free deoxypyridinoline of greater than about 5:1.

3. The method of claim 1, wherein said antibody has a ratio of reactivity toward native free deoxypyridinoline and native free pyridinoline of greater than about 25:1.

4. The method of claim 1, wherein said antibody has a ratio of reactivity toward native free pyridinoline and native free deoxypyridinoline of between about 2:1 and 1:2.

5. The method of claim 1, wherein said reacting includes contacting the urine sample with a solid-phase support having surface-attached peptide-free pyridinoline or deoxypyridinoline for competing with such selected pyridinium crosslinks in a sample.

6. The method of claim 1, wherein said reacting includes contacting the urine sample with a solid-phase support to which said antibody is attached.

7. The method of claim 1, wherein said antibody is a monoclonal antibody.

* * * * *

UNITED STATES PATENT AND TRADEMARK OFFICE
CERTIFICATE OF CORRECTION

PATENT NO. : 5,620,861
DATED : April 15, 1997
INVENTOR(S) : Mary J. Cerelli, Hsin-Shan J. Ju and Robert F. Zuk It is certified that error appears in the above-identified patent and that said Letters Patent is hereby corrected as shown below:

Title page,
Item [56], OTHER PUBLICATION, "Robins, S.P., and Duncan, A.," reference "*Physiophys.*" should be -- *Biophys.* --.

Column 1,
Line 35, "167-173" should be -- 1133-1136 --.

Column 2,
Line 25, delete "1984,";
Line 28, "adult" should be -- adults --;
Line 65, after "Seibel" insert -- et al. --.

Column 3,
Line 4, "bone-metabolism" should be -- bone metabolism --;
Line 22, after "Robins" insert -- et al. --;
Line 56, "with a" should be -- with an --.

Column 4,
Line 58, after "which may" insert -- be --.

Column 5,
Line 3, "membrane" should be -- membranes --;
Line 4, "SPQ" should be -- PSQ --.

Column 8,
Line 56, "Minn." should be -- Maine --.

Column 9,
Line 14, "20852)" should be -- 20852 --;
Line 29, "assays" should be -- assay --.

Column 10,
Line 64, "Dpd" should be -- N-Dpd --;
Line 65, "pyridinoline" should be -- deoxypyridinoline --.

UNITED STATES PATENT AND TRADEMARK OFFICE
CERTIFICATE OF CORRECTION

PATENT NO.    : 5,620,861
DATED         : April 15, 1997
INVENTOR(S)   : Mary J. Cerelli, Hsin-Shan J. Ju and Robert F. Zuk It is certified that error appears in the above-identified patent and that said Letters Patent is hereby corrected as shown below:

Column 11,
After line 51, insert the following paragraph:
-- B4 Affinity Chromatography
The antibody reagent of the invention can also be used in an affinity chromatography matrix, in accordance with standard affinity chromatography methods, for binding and collecting native free pyridinium crosslinks derived from collagen tissues, e.g., by passing pooled urine through such a matrix. For isolation of N-Pyd, an antibody reagent which is specific for N-Pyd is used in the matrix. Alternatively, for isolation of both N-Pyd and N-Dpd, an antibody which binds both with comparable affinities is employed. The native free crosslinks obtained can be further purified by methods described in Examples 1 and 2, as necessary. --

Column 14,
Line 41, "or in a" should be -- or in an --;
Line 44, delete "format like".

Column 15,
Line 1, delete the second "N-Pyd";
Line 5, after "duplicate to" insert -- the -- and after "wells, and" delete "the" and insert -- all --;
Line 6, delete "then";
Line 28, "96 well" should be -- 96-well --;
Line 45, "10.407+0.0.40310x" should be -- 10.407+0.40310x --;
Line 48, after "sample by" insert -- a --;
Line 54, "measure" should be -- measured --.

Column 16,
Line 40, after "allowing the" insert -- N-Dpd or N-Pyd --;
Line 57, insert -- N-Dpd or N-Pyd -- before "analyte" and delete "of interest";
Line 62, delete "vary according to the nature of the analyte and".

Column 17,
Line 18, after "affinity for the" insert -- N-Dpd or N-Pyd --.

UNITED STATES PATENT AND TRADEMARK OFFICE
CERTIFICATE OF CORRECTION

PATENT NO.    : 5,620,861
DATED         : April 15, 1997
INVENTOR(S)   : Mary J. Cerelli, Hsin-Shan J. Ju and Robert F. Zuk It is certified that error appears in the above-identified patent and that said Letters Patent is hereby corrected as shown below:

Column 19,
Line 13, "Immobilon-SPQ (SPQ)" should be -- Immobilon-PSQ (PSQ) --;
Line 57, "Immobilon-SPQ (SPQ)" should be -- Immobilon-PSQ (PSQ ) --;
Line 60, delete "in accordance with the invention".

Column 20,
Line 33, "metastic" should be -- metastatic --;
Line 49, "point" should be -- points --.

Column 21,
Line 28, after "Antibodies" insert a -- . --;
Line 28, "Andibodies Female" should be -- Anditbodies. Female --;
Line 43 "Fetal clone" should be -- FetalClone --;
Line 48, "fetal clone" should be -- FetalClone --.

Column 22,
Line 22, "Filton Co." should be -- Filtron Co. --;
Line 22, "Filton" should be -- Filtron --;
Line 27, "Elution" should be -- Material eluted -- and after "column" delete "material";
Line 30, after "applied onto" insert -- a --;
Line 30, insert -- a -- before "1×18";
Line 38, after "developed with" insert -- a --;
Line 38, insert -- a -- after "with";
Line 47, "(Spectra Por)" should be -- (Spectra/Por from Spectrum Laboratories, Rancho Dominguez, CA). --;
Line 48, "Spectra Por" should be -- Spectra/Por from Spectrum Laboratories, Rancho Dominguez, CA. --;
Line 61, "illustrates" should be -- illustrate --.

Column 23,
Line 4, "an" should be -- a --.

Column 25,
Line 1, "2-pyridylthio)proprionate" should be -- 2-C2-pyridyldithio)propionate --;
Line 3, "uL" should be -- µL --;
Line 4, "ug" should be -- µg --;
Line 11, "ug" should be -- µg --;
Line 12, "4ul" should be -- 4 µl --;
Line 14, "50 ug" should be -- 50 µg -- and "100 µof" should be -- 100 µl of --;

UNITED STATES PATENT AND TRADEMARK OFFICE
CERTIFICATE OF CORRECTION

PATENT NO.   : 5,620,861
DATED        : April 15, 1997
INVENTOR(S)  : Mary J. Cerelli, Hsin-Shan J. Ju and Robert F. Zuk It is certified that error appears in the above-identified patent and that said Letters Patent is hereby corrected as shown below:

Column 25, cont'd,
Line 32, "biotin-X-2,4-dinitrophenol-X-L-lysine" should
be -- biotin-X2,4-dinitrophenyl-X-L-lysine --;
Line 41, "3.8 ug/ml" should be -- 3.8 μg/ml --;
Line 43, "200 ul" should be -- 200 μl --;
Line 46, "150 ul" should be -- 150 μl --;
Line 47, "ug/ml" should be -- μg/ml --;
Line 55, "3000 nMN-Pyd" should be -- 3000 nM N-Pyd --;
Line 56, "NAN3" should be -- NaN$_3$ --;
Line 59, "20 ul/well" should be -- 20 μl/well --;
Line 61, "20 ul/well" should be -- 20 μl/well --;
Line 64, "100 ul/well" should be -- 100 μl/well --;
Line 65, "NAN3" should be -- NaN$_3$ --.

Column 26,
Line 4, "100 uL" should be -- 100 μL --;
Line 12, "sample" should be -- samples --;
Line 20, "HCL" should be -- HCl -- and after "110° C" delete ".";
Line 24 "(y axis)" should be -- (y-axis) --;
Line 34, "0.5 ug/ml" should be -- 0.5 μg/ml --;
Line 44, "NAN3" should be -- NaN$_3$ --.

Column 27,
Line 51, insert -- supernatant -- after "culture";
Line 52, insert -- supernatant -- after "culture".

Column 28,
Line 17, "nitrocellose" should be -- nitrocellulose --;
Line 27, "96 well" should be -- 96-well --;
Line 41, insert -- the -- between "to immunization".

Column 29,
Line 14, "used" should be -- pooled --;
Line 51, "X-2,4-dinitrophenol" should be -- X2,4-dinitrophenyl --;
Line 61, "2-pyridylthio)proprionate" should be -- 2/pyridyldithio)propionate --;
Line 63, "21 uL" should be -- 21 μL --;
Line 64, "260 ug" should be -- 260 μg --.

UNITED STATES PATENT AND TRADEMARK OFFICE
CERTIFICATE OF CORRECTION

PATENT NO.    : 5,620,861
DATED         : April 15, 1997
INVENTOR(S)   : Mary J. Cerelli, Hsin-Shan J. Ju and Robert F. Zuk It is certified that error appears in the above-identified patent and that said Letters Patent is hereby corrected as shown below:

Column 30,
Line 4, "180 ug" should be -- 180 µg --;
Line 6, "4u1" should be -- 4 µl --;
Line 8, "50 ug" should be -- 50 µg --;
Line 21, "200 ul" should be -- 200 µl --;
Line 25, "ul" should be -- µl --;
Line 28, "200 uL" should be -- 200 µl --;
Line 47, "NAN3" should be -- NaN$_3$ --;
Line 52, "125 ul/well" should be -- 125 µl/well --;
Line 60, "150 uL" should be -- 150 µL --.

Column 31,
Line 10, "Selectively" should be -- Selectivity --;
Lines 43-46, delete the paragraph.

Signed and Sealed this

Sixteenth Day of December, 2003

JAMES E. ROGAN
*Director of the United States Patent and Trademark Office*